US008269966B2

(12) United States Patent
Gruler

(10) Patent No.: US 8,269,966 B2
(45) Date of Patent: Sep. 18, 2012

(54) FLUORESCENCE METER

(75) Inventor: Roman Gruler, Rottweil (DE)

(73) Assignee: Qiagen Lake Constance GmbH, Stockach (DE)

(*) Notice: Subject to any disclaimer, the term of this patent is extended or adjusted under 35 U.S.C. 154(b) by 335 days.

(21) Appl. No.: 11/885,068

(22) PCT Filed: Mar. 3, 2006

(86) PCT No.: PCT/EP2006/001952
§ 371 (c)(1), (2), (4) Date: Feb. 26, 2008

(87) PCT Pub. No.: WO2006/092317
PCT Pub. Date: Sep. 8, 2006

(65) Prior Publication Data
US 2008/0144028 A1    Jun. 19, 2008

(30) Foreign Application Priority Data
Mar. 3, 2005  (DE) .................. 10 2005 010 981

(51) Int. Cl.
*G01J 3/30* (2006.01)
(52) U.S. Cl. ....................... 356/318; 356/402
(58) Field of Classification Search ................. 356/318, 356/402
See application file for complete search history.

(56) References Cited

U.S. PATENT DOCUMENTS

| | | | |
|---|---|---|---|
| 4,087,685 A | 5/1978 | Froot | |
| 4,841,156 A | 6/1989 | May et al. | |
| 5,108,932 A * | 4/1992 | Wolfbeis | 436/124 |
| 5,127,730 A * | 7/1992 | Brelje et al. | 356/318 |
| 5,963,314 A * | 10/1999 | Worster et al. | 356/237.2 |
| 5,972,716 A | 10/1999 | Ragusa et al. | |
| 6,141,096 A * | 10/2000 | Stern et al. | 356/318 |
| 6,462,345 B1 * | 10/2002 | Simon et al. | 250/458.1 |
| 6,611,326 B1 | 8/2003 | Yakovlev et al. | |
| 7,063,996 B2 * | 6/2006 | Ishii et al. | 438/28 |
| 2003/0004418 A1 | 1/2003 | Marmorstein | |
| 2006/0256338 A1 * | 11/2006 | Gratton et al. | 356/417 |

FOREIGN PATENT DOCUMENTS

| | | |
|---|---|---|
| WO | WO 84/00609 A | 2/1984 |
| WO | WO 00/30528 | 6/2000 |
| WO | WO 03/077008 | 9/2003 |

* cited by examiner

*Primary Examiner* — Tarifur Chowdhury
*Assistant Examiner* — Isiaka Akanbi
(74) *Attorney, Agent, or Firm* — Shlesinger, Arkwright & Garvey LLP

(57) ABSTRACT

Disclosed is a fluorescence meter for analyzing a sample, comprising a main beam path and at least one optical module. The fluorescence meter is embodied so as to provide at least one electromagnetic beam for exciting the sample and receive at least one electromagnetic beam emitted by the sample, at least some sections of at least two of the electromagnetic beams being located on one plane while extending along the main beam path.

21 Claims, 18 Drawing Sheets

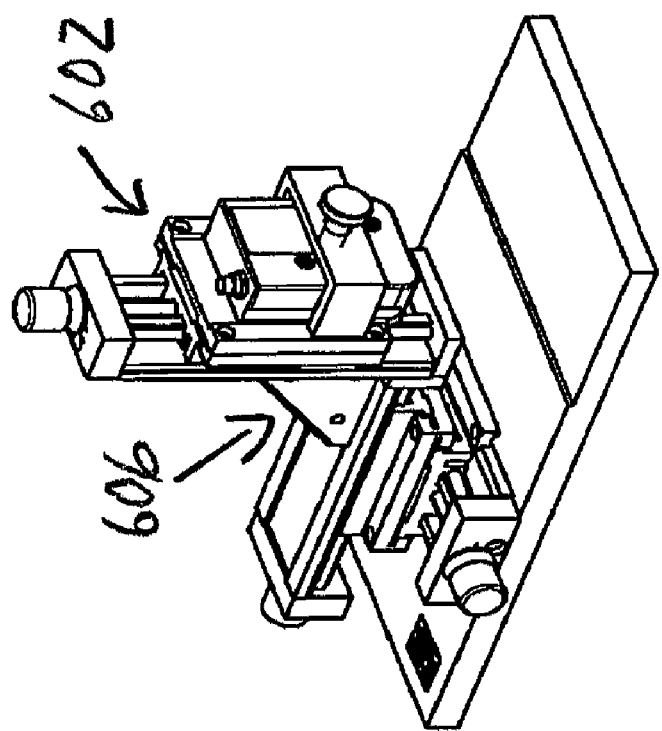
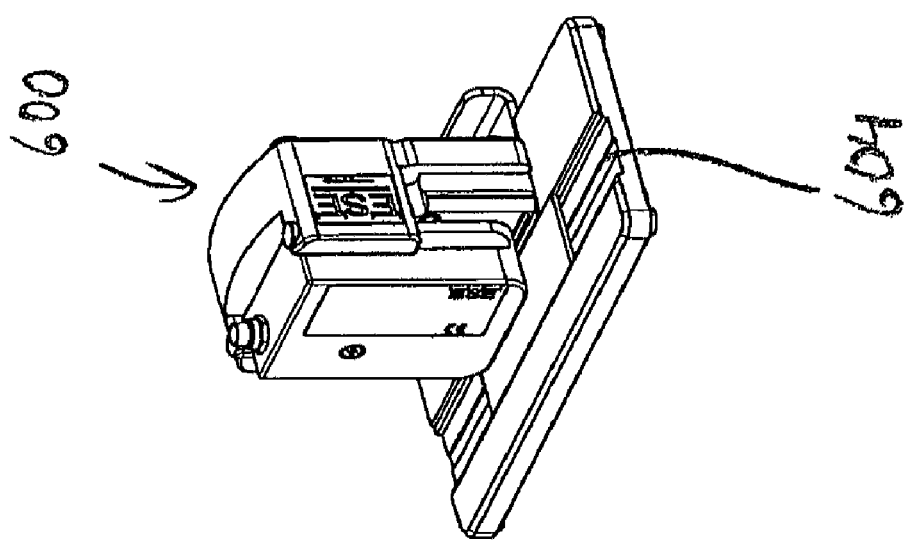
Fig. 24

FLUORESCENCE METER

FIELD OF THE INVENTION

The invention relates to a fluorescence meter for investigating a specimen, a process for investigating a specimen, a computer program with program coding means and a computer program product with program coding means.

BACKGROUND OF THE INVENTION

Fluorimeters for investigating specimens and objects are known. However, known fluorimeters are generally constructed so as to have only a low depth of focus and therefore have to be positioned at a precise distance from the plane which is to be investigated.

Against this background the invention proposes a fluorescence meter, a method, a computer program and a computer program product.

OBJECTS AND SUMMARY OF THE INVENTION

The fluorescence meter according to the invention for investigating a specimen has a main optical path and at least one optical module and is constructed so as to provide at least one electromagnetic beam intended to excite the specimen, and to receive at least one electromagnetic beam emitted by the specimen, at least two of these electromagnetic beams being located at least partly in one plane and extending along the main optical path. With this fluorescence meter it is now possible to obtain measurements with a high depth of focus when investigating specimens.

The fluorescence meter according to the invention is a sensitive, tolerant and small measuring instrument which can be used to carry out measurements in all kinds of specimens.

Thus, measurements may be carried out both on surfaces and in thin layers, with test strips and in so-called PCR tubes.

The fluorescence meter according to the invention has at least one, particularly two, sources for providing electromagnetic beams and is constructed for example for the simultaneous measurement of two fluorescent dyes.

The fluorescence meter has at least one monitor diode, while preferably each source is associated with one monitor diode for monitoring the light output.

The meter is designed so that ambient light compensation can be carried out. This means that initially measurements are taken with the source or LED switched off and then with the source switched on. The amount of extraneous light can then be determined by comparing the two results.

Preferably, the at least one source is encapsulated in an encapsulation, which may consist of an aluminium block. The encapsulation preferably has an opening serving as a shutter.

Typically, the at least one monitor diode is provided for monitoring one of the sources and an optical module is arranged between this source and the monitor diode.

An optical path from the source to the at least one monitor diode is advantageously constructed such that no extraneous light can affect the measurement.

The fluorescence meter can be constructed so as to carry out simultaneous measurement of a fluorescence and a reflection.

In the fluorescence meter, the optical modules, the monitor diode, detectors and/or sources are provided in a housing.

In the fluorescence meter the housing comprises for example a main channel for the main optical path and at least one secondary channel branching off the main channel for a secondary optical path.

The fluorescence meter is preferably constructed so as to provide at least one electromagnetic beam provided as a positioning beam and comprises as further features filters, beam splitters and/or mirrors as optical modules. In addition, light traps may be provided in the housing of the meter.

In a preferred embodiment the meter comprises a device for stabilising an output of an electromagnetic beam produced by the at least one source.

This device is typically associated with the monitor diode, which is constructed so as to continuously measure a radiant output from the at least one source.

The device is preferably constructed so as to eliminate any deviation of the radiant output from a desired value in real time.

In the fluorescence meter, the device for measuring the beam output of an electromagnetic beam which is emitted by the at least one source and strikes a first location is preferably provided, wherein the electromagnetic beam between the at least one source passes through a first optical module, e.g. a band-pass filter, with at least one optical property, and wherein part of the electromagnetic beam which is to be measured between the at least one source and the monitor diode passes through a second optical module, e.g. a band-pass filter, which has substantially the same at least one optical property as the first optical module.

An adaptor according to the invention with a fluorescence meter according to the invention is constructed such that it can be used to take measurements both on microscope slides or similar specimens or specimen holders, which may not be transparent, and also on dishes, as a result of the spacing tolerance provided.

A process according to the invention is used for examining a specimen with a fluorescence meter, particularly with a fluorescence meter according to the invention, which comprises a main optical path and at least one optical module, wherein the specimen is excited by at least one electromagnetic beam provided by the fluorescence meter and at least one electromagnetic beam emitted by the specimen is received by the fluorescence meter, at least two of these electromagnetic beams being guided at least partly in one plane along the main optical path.

In the process, at least one electromagnetic beam provided as the positioning beam and at least one electromagnetic beam provided as the measuring beam are provided, for example, by means of the fluorescence meter.

The method can be used to examine a surface of a component, a specimen in a test strip or an eye. Measurements in thin layers are also possible.

During the examination of an eye, an illumination source of the fluorescence meter may provide a background illumination for the marking, the background illumination causing the pupil of the eye to become smaller during the examination so as to make positioning easier.

During the process, a radiant output of an electromagnetic beam produced by at least one source is preferably stabilised by a device.

For example, the radiant output of the at least one source is measured continuously by a monitor diode of the device.

Thus, the radiant output of an electromagnetic beam emanating from the source and striking a first location may be measured, the electromagnetic beam along a first optical path passing through a first optical module with at least one optical property, e.g. a band-pass filter, and wherein part of the electromagnetic beam which is to be measured is guided along a second optical path branching off the first optical path, on which the mounting or photodiode is arranged, the second optical path comprising a second optical module which has the same optical property as the first optical module, for example a band-pass filter.

Moreover, in the process, ambient light compensation may be carried out by comparative measurement with the source or LED switched on and off.

The fluorescence meter is preferably constructed so as to excite fluorescence in the specimen with the at least one electromagnetic beam provided for exciting the specimen, so that the specimen emits at least one fluorescent electromagnetic beam of a wavelength range. In addition, reflection can be excited in the specimen by the at least one electromagnetic beam, so that the specimen emits at least one reflective electromagnetic beam of a wavelength range. The electromagnetic beam emitted excites material in the specimen and as a result of an interaction of this kind electromagnetic beams produced in the specimen are emitted.

According to a further feature the fluorescence meter is suitable for the parallel measurement of at least two electromagnetic beams emitted by the specimen. These at least two electromagnetic beams are received and examined separately in the fluorescence meter. For this purpose the electromagnetic beams are spectrally separated and detected independently of one another by sensors or detectors which are sensitive to particular spectral ranges of electromagnetic beams. Sensors or detectors of this kind may be photodiodes, for example.

Irrespective of whether the at least one electromagnetic beam emitted by the specimen is produced by fluorescence or reflection, it can be detected by the fluorescence meter. Accordingly, the fluorescence meter is also suitable for the parallel measurement of fluorescence and reflection of the specimen.

In a preferred embodiment the fluorescence meter is designed to examine a specimen with at least two electromagnetic beams. Optical modules or elements of the fluorescence meter are constructed and arranged such that at least one electromagnetic beam with at least one frequency range is emitted simultaneously. When this at least one electromagnetic beam strikes the specimen, an interaction occurs as a result of the excitation of material in the atomic and/or molecular range, so that the at least one electromagnetic beam is emitted by the sample in at least one frequency range. This at least one electromagnetic beam is received and investigated by the fluorescence meter. The fluorescence meter can compensate any changes in the excitation output caused by spectral drift of the light source, as identical conditions are present in the monitoring and excitation optical path.

Optical modules of the fluorescence meter may be constructed and arranged such that optical paths of an electromagnetic beam provided for excitation of the specimen and an electromagnetic beam emitted by the specimen are located at least partly in one plane and thus extend along a main optical path of the fluorescence meter which is consequently confocal. The individual electromagnetic beams may extend coaxially with respect to one another in the optical path.

For carrying out the investigation or measurement of the specimen the fluorescence meter is constructed, for example, such that it provides at least one electromagnetic beam as a positioning beam and at least one electromagnetic beam as a measuring beam. These may be located in an optical housing and have a common main optical path. With the positioning beam it is possible to position the fluorescence meter so as to take account of a suitable distance and/or angle with respect to the specimen. Accordingly, the fluorescence meter is also suitable for distance measurements, for example. The use of the positioning beam for aligning or positioning the fluorescence meter and/or the measuring beam is advantageous both with surfaces and with at least partially transparent specimens extending three-dimensionally, so that the measuring beam can be focused precisely on a desired point of the specimen for investigation. There is no need for any shutter or aperture shutter in front of the sensor or photodiode in order to carry out the positioning using the positioning beam.

As a result of the different transit distances of the optical paths of the measuring beam and positioning beam different depths of focus are obtained and because of the positioning of the detector for the positioning beam behind the detector for the measuring beam, resulting in a longer transit distance for the positioning beam, during rough positioning greater variations in the signal are obtained in the positioning beam than in the measuring beam. Thus, the positioning beam can be used to carry out accurate positioning as, in the event of any deviation from the ideal position, this deviation results in a greater change in the positioning beam than in the measuring beam.

The fluorescence measuring device preferably has a confocal optical device and at least one secondary optical path branching off the main optical path, while the at least one optical module designed to influence an electromagnetic beam is arranged in at least one of these optical paths, the main optical path and/or at least one secondary optical path branching off it. It is thus possible to manipulate electromagnetic beams produced or prepared by the fluorescence meter, which are intended for the investigation of the specimen. Similarly, the fluorescence meter can be used to modulate electromagnetic beams emitted by the specimen by means of the at least one optical module within the optical paths.

The at least one optical module may be constructed so as to filter a spectral range of an electromagnetic beam striking this optical module. The at least one optical module may also be constructed so as to alter a direction of a spectral range of an electromagnetic beam striking this optical module. The at least one optical module is therefore permeable to certain wavelengths of electromagnetic radiation and impermeable to certain wavelengths of electromagnetic radiation. Moreover, the at least one optical module may be constructed such that a first specific frequency range or a first specific wavelength of the electromagnetic radiation is reflected at a certain angle. A second frequency range or a second wavelength of the electromagnetic radiation is reflected by the at least one optical module, optionally at a second angle, or is not reflected at all.

The at least one optical module of the fluorescence meter may be arranged within at least one of the optical paths in such a way that it deflects a direction of a spectral range of the electromagnetic path at an angle of 90°, for example. If for example it is envisaged that the fluorescence meter produces two electromagnetic beams of different wavelengths, these may be combined by the at least one optical module in a common optical path, so as to reach the specimen simultaneously. It is also possible to separate or spectrally filter electromagnetic beams which have different wavelength ranges and extend within one optical path, through a number of optical modules which are arranged at different points within the optical path, so that different wavelength ranges of the electromagnetic beams can be investigated separately at different points.

The fluorescence meter is preferably constructed so that the specimen is impacted simultaneously by at least two electromagnetic beams. These two electromagnetic beams may have different frequencies or wavelengths and may thus excite the specimen differently in terms of energy and/or spectrum. Similarly, the fluorescence meter may be constructed so as to receive electromagnetic beams with at least two spectral ranges or wavelengths simultaneously from the specimen and analyse these at least two spectral ranges or wavelengths of the electromagnetic beams separately.

The specimen to be investigated may consist of a number of substances and materials which may react differently to electromagnetic beams of different wavelengths. As it is possible to investigate a plurality of electromagnetic beams simultaneously in the present fluorescence meter, a number of qualitative properties of the specimen or a number of qualitative or quantitative properties of the specimen can be determined simultaneously. The electromagnetic beams to be provided by the fluorescence meter for exciting the specimen and also the electromagnetic beams emitted by the specimen and to be detected by the fluorescence meter are substantially within the visible range or in the ultraviolet range.

According to one possible embodiment of the invention it is envisaged that at least one optical module is constructed as a dichroic mirror. Dichroic mirrors of this kind have a plurality of layers of, for example, dielectric materials with different refractive indices. The dichroic mirrors are designed to spectrally divide up an electromagnetic beam or a light beam with different frequency ranges according to the number and composition of the layers. A first wavelength of the electromagnetic beam is reflected by the dichroic mirror, whereas this dichroic mirror is permeable to electromagnetic beams of a different wavelength. The individual layers of the dichroic mirror may be applied during its manufacture by ion plating, for example. Thus, the individual layers are sharply separated from one another and the dichroic mirror thus has a steep filter edge. In order to achieve a desired spatial subdivision for the investigation of an electromagnetic beam, a plurality of dichroic mirrors of this kind may be arranged one behind the other within one optical path, so that a frequency range of the electromagnetic beam first of all passes through a dichroic mirror and only downstream thereof is reflected by a subsequent dichroic mirror and branched off or coupled out in the direction of another optical path, for example, for investigation.

In order to prepare the at least one beam for investigating the specimen, the fluorescence meter typically has at least one electromagnetic source or light source which may take the form of an LED (Light Emitting Diode) or laser, for example.

An electromagnetic beam which may have a specific wavelength is emitted by the electromagnetic source, so that this electromagnetic beam passes through one of the secondary optical paths. From this one secondary optical path the electromagnetic beam is coupled into the main flow path, optionally while being spectrally broken up by one of the dichroic mirrors. The fluorescence meter is arranged or has to be arranged relative to the specimen which is to be investigated, such that the main optical path crosses the specimen or a desired area of the specimen to be investigated. The fluorescence meter may be aligned relative to the specimen by means of the positioning beam. The positioning beam may also be used to suitably adjust or focus, onto the specimen or the area of the specimen, a measuring beam which is intended for the actual investigation and hence excitation of the specimen. Equally, in a fluorescence meter with two sources, one of these sources is to be used to produce the positioning beam and the other source is to be used to produce the actual measuring beam. If for example a reference dye is applied to or mixed with a specimen, the optimum position for the actual measurement can be determined by means of the positioning beam.

In particular, LEDs with Lambertian radiation characteristics having a die are suitable as the at least one electromagnetic source for the fluorescence meter. The die is a small plate of semiconductor substrate. Moreover, a frequency spectrum of the electromagnetic beam emitted by the LED or the die must be taken into account. An LED may be selected such that it emits or radiates only electromagnetic radiation or light of a certain frequency, for example in the ultraviolet range. If the LED radiates electromagnetic radiation of a broad frequency range it is possible to filter out a desired frequency range through the at least one optical module. Thus the material of the specimen may be excited by a suitable frequency of the electromagnetic beam.

Furthermore, the at least one optical module may be constructed as an interference band-pass for spectrally breaking down or filtering the at least one electromagnetic beam. An interference band-pass of this kind is permeable to first wavelength ranges of the at least one electromagnetic beam and not permeable to second wavelength ranges of this electromagnetic beam. With the interference band-pass it is possible to prepare, from a broad frequency spectrum of an electromagnetic beam, a specific frequency range for exciting the specimen. Similarly, using the interference band-pass it is possible to filter out, from an electromagnetic beam, a spectral range which is intended for investigation or analysis.

An electromagnetic beam emitted by the specimen and thus received by the fluorescence meter is spectrally split within the main optical path, according to a preferred embodiment, so that specific spectral ranges of this electromagnetic beam are branched off into secondary optical paths by dichroic mirrors. Sensors or detectors are arranged in these secondary optical paths, which are designed to carry out both qualitative and quantitative optical investigation of the electromagnetic beam received, within certain spectral ranges. The sensors may be single, dual or multi-channel sensors. The sensors are constructed for example as photodiodes.

For filtering or breaking down an electromagnetic beam the fluorescence meter may also comprise a high-pass relay constructed from a plurality of optical modules such as dichroic mirrors, interference band-passes, lenses, shutters, filters and the like. Low-pass filters may be provided in the secondary optical paths.

The at least one electromagnetic source or light source of the fluorescence meter may generate an electromagnetic beam with a time-limited length of the order of a few ms to several hundred ms. Thus it is possible to carry out short-term investigations of the specimen. If the specimen consists of delicate, e.g. organic material, a chemical composition of this material is virtually unaffected by the very brief action of the electromagnetic beam. The specimen is treated gently as a whole throughout the investigation.

In one possible embodiment the fluorescence meter has a housing in which a number of optical modules are to be arranged in modular fashion or in which a number of optical modules are arranged in modular fashion. Thus it is possible to target the design of the fluorescence meter to specific investigations of specific specimens of specific material properties or compositions, or to equip the meter with optical modules, so that the specimens can be individually acted upon by electromagnetic beams of specific wavelengths. At the same time at least one electromagnetic beam with an expected wavelength emitted by one of the specimens is to be investigated.

The housing of the fluorescence meter may comprise a main channel for electromagnetic beams which extend within the main optical path, and at least one secondary channel branching off this main channel, in which electromagnetic beams of a secondary optical path extend. These channels, i.e. the main channel and the minimum of one secondary channel, are provided on the inner wall, for example, with notches or grooves in which the optical modules can easily be inserted in modular fashion and if necessary taken out again.

The dichroic mirrors may be arranged at branches or intersections of the main channel and the minimum of one secondary channel branching off it. The main channel and the at least one secondary channel may intersect, for example, at an angle of 90°, so that the main optical path within the main channel intersects with at least one secondary optical path of the secondary channel, again at an angle of 90°, for example. For this purpose it is envisaged that dichroic mirrors should be arranged within the housing such that they are inclined at an angle of 45° or arranged diagonally relative to the main channel and hence to the main optical path and relative to the secondary channel and correspondingly to the secondary optical path. Thus, an electromagnetic beam extending within the secondary channel may be deflected by the dichroic mirror at an angle of 90° and thus coupled into the main channel in the direction of the main optical path. Accordingly, an electromagnetic beam extending in the main channel is to be coupled by the dichroic mirror out of the main channel, and hence the main optical path, and into the secondary channel and hence the secondary optical path.

In one possible embodiment it is envisaged that a housing of the fluorescence meter, which is intended for modular accommodation of optical components, is made from an injection moulded plastics part. Alternatively, the housing of the fluorescence sensor is to be produced by silicon casting from a blank produced by CNC milling. An injection moulding process can also be used.

The fluorescence meter may be intended or constructed for examining a patient's eye. Using this fluorescence meter an area on or within the eye or eyeball is examined optically. The fluorescence meter and hence the measuring beam for the actual examination have to be aligned with the positioning beam, while exciting the region of the eye, so that the measuring beam is focused precisely into the desired area of the eye. Electromagnetic radiation emitted from this area is to be detected by the fluorescence meter and examined, taking account of specific wavelength ranges.

The fluorescence meter may be constructed such that at least one electromagnetic beam with a fluorescence wavelength which is to be detected and at least one electromagnetic beam with an excitation wave have the same focal point on or inside the specimen by confocal construction of at least one of the optical paths for the at least one electromagnetic beam provided as a measuring beam. Suitable guiding of at least one electromagnetic beam, irrespective of whether it is produced by the fluorescence meter or emitted by the specimen, is ensured by a suitable arrangement of the optical modules within the at least one optical path.

According to one embodiment, the at least one fluorescence wavelength which is to be detected, of an electromagnetic beam emitted by the eye, for example on or inside the cornea which is to be examined, and the at least one excitation wavelength of the electromagnetic beam for exciting the eye have the same focal point on the cornea of the eye. Naturally it is possible to adjust the fluorescence meter such that other areas of the eye can also be examined. With a suitable choice of an excitation wavelength for the at least one electromagnetic beam, attention must be paid to the material which is to be excited within the specimen, so that electromagnetic beams with suitable physical parameters such as wavelength, intensity and the like are emitted for the investigation. Moreover, when designing the fluorescence meter it is important to bear in mind how the electromagnetic excitation beam and the electromagnetic beam emitted behave as they travel to the part of the specimen which is to be investigated and back again to the fluorescence meter, so as to provide a suitable focal point. This focal point is to be gauged for the measuring beam by positioning using the positioning beam.

The fluorescence meter is constructed, for example, so as to provide electromagnetic beams of different wavelengths, for example from 260 nm to 900 nm. The measuring device may be used both in the UV range and in the NIR or VIS range. It is also possible to use UV-LEDs. A suitable wavelength depends on the material composition and/or the desired fluorescence effects of the specimen which are to be measured. The electromagnetic beams, for example in the ultraviolet range, with a desired wavelength are deliberately produced by a suitable choice of the electromagnetic source and/or a suitable choice of the optical modules such as interference band-passes and/or dichroic mirrors.

According to a further feature the fluorescence meter may have a marking in the form of a cross or a corresponding orientation point, which is provided in order for the eye to concentrate on this marking during examination. In addition, the fluorescence meter may have a source of illumination for providing backlighting for the marking and at the same time to cause the pupil to contract during the examination. Thus, in order to perform the examination, it is envisaged that the patient should direct his vision onto the marking. The actual examination in which the measuring beam is first to be adjusted via the positioning beam and the measurement with the measuring beam is to be provided in order to excite a region of the eye, can be carried out in a short time. The eye is only acted upon by these electromagnetic beams, i.e. by the positioning beam and the measuring beam, for a period of the order of a few milliseconds or a few tens of milliseconds, which means that irritation or damage to the eye can be ruled out. The light output is so small that no damage can occur.

The fluorescence meter may have a device for stabilising a radiant output of an electromagnetic beam produced by the at least one electromagnetic source. This device may be provided with a monitor or photodiode for this purpose, with which the radiant output of the at least one electromagnetic source is continuously measured. Moreover, using this device, it is also possible to measure a wavelength or a wavelength range of the electromagnetic radiation emitted by the electromagnetic source. A possible deviation of the radiant output from a desired value can be eliminated by suitable adjustment in interaction between the device and the electromagnetic source in real time.

In this case the device for the fluorescence meter is intended to measure the radiant output of an electromagnetic beam emitted by the at least one source and striking the specimen at a first location, while the electromagnetic beam between the at least one electromagnetic source passes through a first optical module, e.g. a band-pass filter, having at least one optical property, wherein part of the electromagnetic beam which is to be measured between the electromagnetic source and the monitor diode passes through a second optical module, e.g. a band-pass filter. It is envisaged that the first and second optical modules should have the same optical properties. This ensures that the electromagnetic beam intended for the actual examination of the specimen and the area branching off from this electromagnetic beam, which is examined by the device, pass through substantially the same physical route and arrive at the specimen which is to be investigated, similarly modified or unmodified, so that a light or radiant output which is constant over time can be ensured with the monitor diode.

The apparatus according to the invention for examining a specimen is equipped with at least one fluorescence meter. The apparatus typically has a specimen holder which is constructed so as to hold both the specimen to be examined and to receive the at least one fluorescence meter.

In known apparatus for examining specimens it is envisaged that a specimen holder is located inside a measuring apparatus. In the apparatus according to the invention, by contrast, the fluorescence meter, i.e. a device for optical investigation, is located inside the specimen holder of the apparatus. The specimen holder is preferably constructed so that different fluorescence meters can be put into it and taken out again, with the result that, thanks to this exchangeability, different specimens can be examined under different conditions, i.e. by providing different electromagnetic beams of different wavelengths or intensities.

According to a further feature the apparatus is equipped with a manual control device which is designed to read out data from the fluorescence meter. The apparatus and the manual control device may be equipped with an interface through which it is possible to transfer data to an external computing unit. Thus, investigation of the specimen, which includes controlling the fluorescence meter and evaluating the electromagnetic beams emitted by the specimen, is possible both with the manual control device, which may comprise for this purpose a suitable display and a suitable keyboard, and also with the computing unit attached to the apparatus. In this way it is possible to carry out automatic, computer-aided examination of the specimen and hence fluorescence measurement. It is also possible for the apparatus to comprise, for example, inside the manual control device, a computing unit or a computer for control and evaluation. During evaluation, electromagnetic beams, e.g. reflected beams, detected during the examination can be eliminated.

The apparatus or the specimen holder of the apparatus may be constructed so that the apparatus can accommodate two fluorescence meters which are arranged relative to one another such that their main optical paths are oriented parallel to one another, so that these two main optical paths can be adjusted individually and positioned at a spacing from the specimen.

According to a preferred feature the apparatus can be used to carry out computer-aided automated simulation of a fluorescence measurement. Moreover, the apparatus may have a stepping motor by means of which a movable and fixable connection can be created between the at least one fluorescence meter and the specimen holder and/or the manual control device. Using this stepping motor it is possible to position the specimen and the at least one fluorescence meter in up to three spatial directions x, y and z relative to one another.

Preparation of an actual measurement using the measuring beam can be carried out using the positioning beam. As soon as a suitable positioning or alignment of the fluorescence meter relative to the specimen has been determined by means of the positioning beam, the stepping motor can align the specimen and the at least one fluorescence meter relative to one another on the basis of the data thus obtained, so that the actual examination of the specimen can be carried out under optimum conditions in automatic and/or computer-aided manner. Furthermore, the apparatus can also carry out an equally computer-aided motorised calibration of the at least one fluorescence meter.

The fluorescence meter can be used in numerous fields. Thus it is suitable for optical examination of production processes. By means of the interface on the fluorescence meter or the apparatus it is possible to communicate with technical equipment which can be controlled directly or indirectly using the measurements taken by the fluorescence meter.

In the process according to the invention for examining a specimen with a fluorescence meter, which comprises a main optical path and at least one optical module, the specimen is excited by at least one electromagnetic beam provided by the fluorescence meter and at least one electromagnetic beam emitted by the specimen is received by the fluorescence meter. At least two of these electromagnetic beams are guided at least in part in a plane along the main optical path. This process can be carried out with the fluorescence meter according to the invention, according to a preferred feature.

According to a preferred feature, at least two electromagnetic beams are provided for investigating the specimen using the fluorescence meter. As a result, fluorescence and reflection of the specimen can be measured in parallel. Optical paths of an electromagnetic beam provided for measuring fluorescence and of an electromagnetic beam provided for measuring reflection are guided at least in part in one plane along a main optical path of the fluorescence meter. During the process, at least one wavelength range is filtered out of the at least one electromagnetic beam by means of suitable optical modules, so that for the investigation of the specimen an electromagnetic beam is provided for exciting the specimen with a suitable frequency range, e.g. in the ultraviolet range. Also, with the at least one optical module from an electromagnetic beam emitted from the specimen, a wavelength range of interest for the examination is supplied for analysis to a sensor or detector.

In one possible variation of the process, at least one electromagnetic beam intended as a positioning beam and at least one electromagnetic beam intended as a measuring beam are provided by means of the fluorescence meter. This positioning beam can be used to position the fluorescence meter at a suitable distance from and at a suitable angle to the specimen which is to be examined. Similarly, the actual measuring beam may be aligned using the positioning beam. The positioning beam and the measuring beam for a particular type of comparable specimens which are to be investigated may be matched to one another in wavelength so as to assist the positioning process.

To make the measurement easier it is possible for a patient to fix his eye on a marking or an orientation point, e.g. in the form of a cross, inside a fluorescence meter. The eye is ideally aligned so that the electromagnetic beams provided for the examination reach desired areas on or inside the eye and are focused there. The marking may be illuminated by an illumination source of the fluorescence meter. In this way the patient's eye can be better concentrated on the marking. The illumination source also ensures that the pupil of the eye is contracted during examination and positioning is thus improved, so that the results of the fluorescence measurement are improved.

It is also possible for the process to be carried out simultaneously with two fluorescence meters which are arranged relative to one another such that their main optical paths are oriented parallel to one another and are spaced from one another by the distance between the eyes of a person to be examined, so that during the examination both eyes of this person can be examined.

The process can be carried out automatically using a computer or a corresponding computing unit. It is also possible to simulate the fluorescence measurement. Carrying out the process with the aid of a computer means that all the aspects of the fluorescence measurement and automated handling of the fluorescence meter can be included. Thus, electromagnetic beams intended for exciting the specimen can be prepared in a suitable frequency range with a suitable output. Alignment of the at least one fluorescence meter relative to the specimen with the aid of the positioning beam or corresponding alignment of the at least one measuring beam relative to the specimen can also be carried out with computer assistance. A specimen holder which accommodates the at least one fluorescence meter and the specimen is equipped with a stepping motor which, during the process, positions the fluorescence meter and the specimen relative to one another in up to three spatial directions, providing a suitable distance and setting a suitable angle. In addition, the fluorescence meter is also calibrated by computer during the process. The evaluation of the measured data can be carried out with the aid of a computer.

The computer program according to the invention with program coding means is designed to perform all the steps of the process according to the invention if the computer program is run on a computer or a corresponding computing unit, particularly a computing unit of the apparatus according to the invention.

The computer program product according to the invention with program coding means stored on a computer-readable data carrier is designed to perform all the steps of the process according to the invention when the computer program is run on a computer or on a corresponding computing unit, particularly a computing unit of the apparatus according to the invention.

Further features and advantages of the invention will become apparent from the description and the accompanying drawings.

It should be understood that the features mentioned above and those explained hereinafter can be used not only in the particular combination specified but also in other combinations or on their own, without departing from the scope of the present invention.

BRIEF DESCRIPTION OF THE DRAWINGS

The invention is schematically illustrated in the drawings by means of an embodiment by way of example and is described in detail hereinafter with reference to the drawings.

FIG. 8a shows a fifth embodiment of a confocal fluorescence meter, shown schematically.

FIG. 8b shows details of the confocal fluorescence meter shown in FIG. 8a.

FIGS. 21 to 27 show other possible applications.

DETAILED DESCRIPTION OF THE INVENTION

Figure 1:
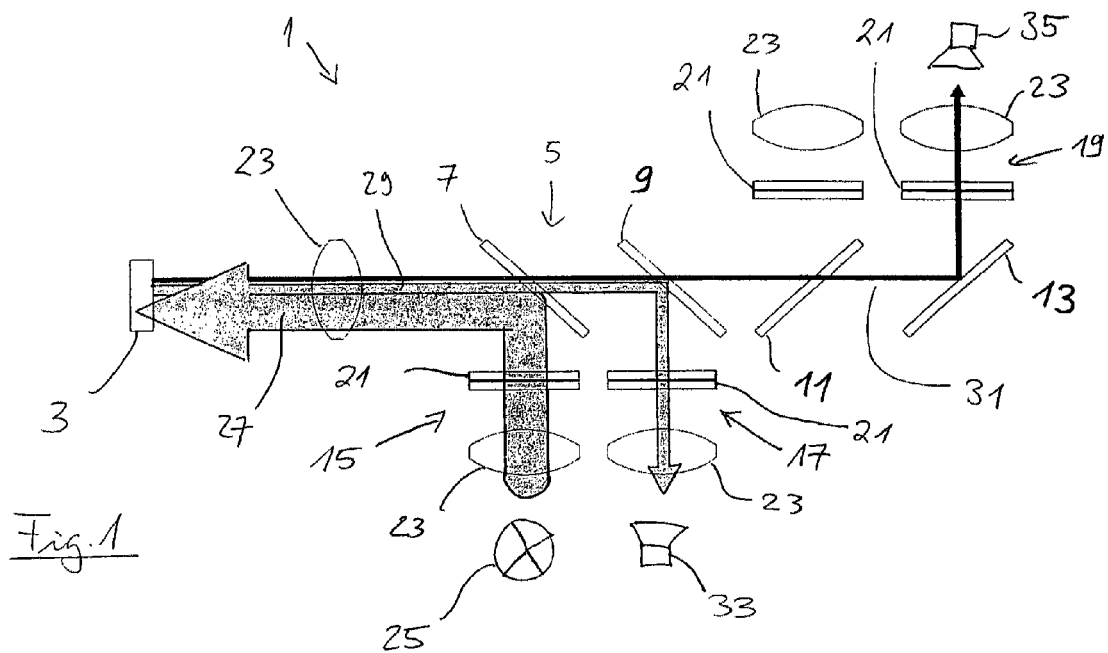
FIG. 1 shows a first embodiment of a fluorescence meter according to the invention, shown schematically.

The Figures are described cohesively and in overlapping fashion, the same reference numerals denoting identical components.

Figure 2:
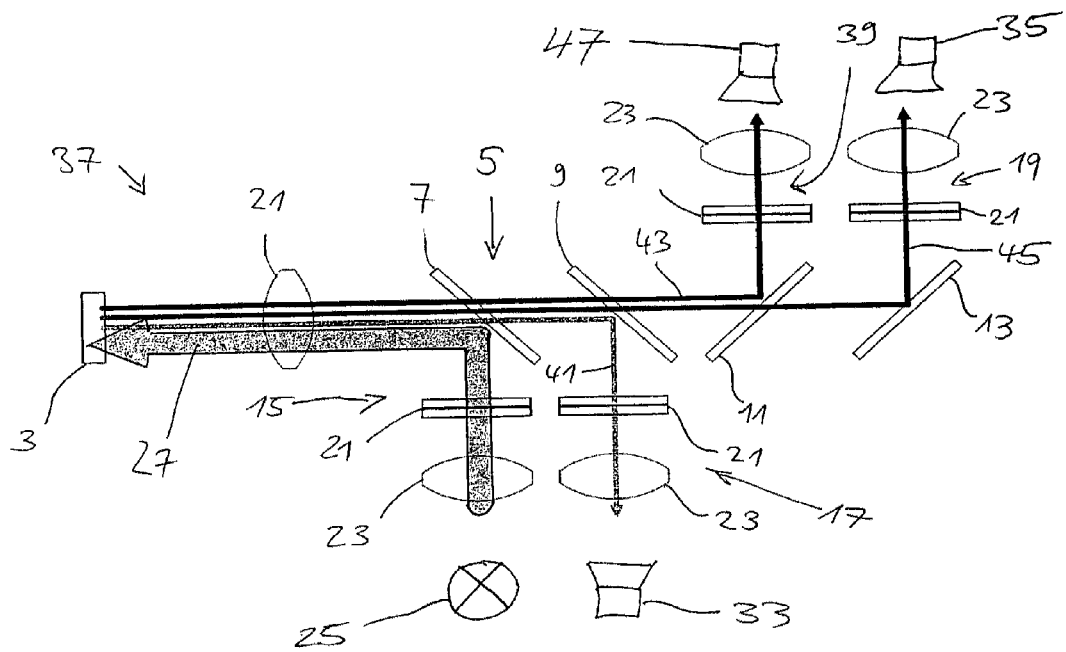
FIG. 2 shows a second embodiment of the fluorescence meter, shown schematically.
Figure 3:
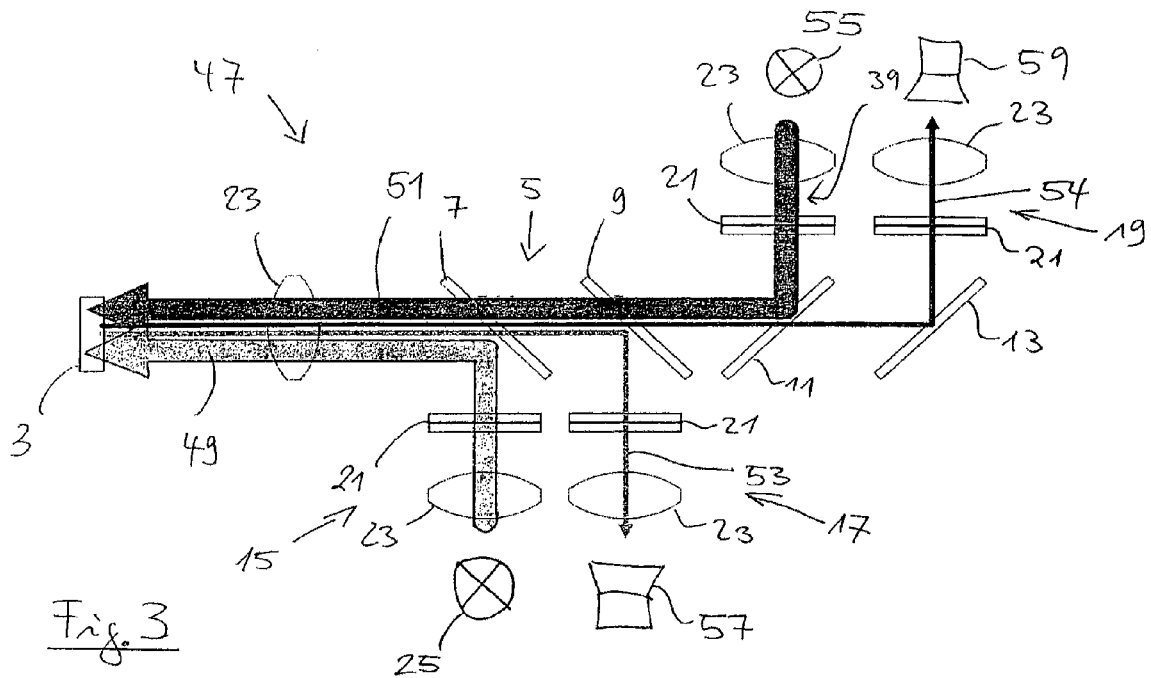
FIG. 3 shows a third embodiment of the fluorescence meter, shown schematically.

FIGS. 1 to 3 show schematic views of three possible embodiments of confocal fluorescence meters 1, 37, 47, with the associated operating options described in each case.

FIG. 1 shows a first embodiment of a fluorescence meter 1 which is constructed so as to produce an electromagnetic beam suitable for exciting 27 a specimen 3. A detection of at least two electromagnetic beams emitted by the specimen 3, in this case a first fluorescent beam 29 and a second fluorescent beam 31, is also possible with the fluorescence meter.

The fluorescence meter 1 comprises in a main optical path 5 beam splitters 7, 9, 11 and 13 in the form of dichroic mirrors. Band-passes 21 are provided in secondary optical paths 15, 17 and 19. In addition, lenses 23 are arranged in the main optical path 5 and in the secondary optical paths 15, 17, 19.

In the first secondary optical path 15, viewed from the left, there is additionally provided an electromagnetic source 25 for providing electromagnetic radiation, from which an excitation 27 emanates, as indicated by a broad arrow.

The first beam splitter 7 is provided so as to direct the excitation 27 from the secondary optical path 15 into the main optical path 5, the first beam splitter 7 does not totally reflect a wavelength of the excitation 27. As a result, electromagnetic radiation emitted by the specimen 3 is directed out of the main optical path 5 to a small extent by the first beam splitter 7 and the second beam splitter 9 and to a large extent by the fourth beam splitter 13. A spectral configuration of the band-passes 21 and of the beam splitters 7, 9, 11, 13 in the first secondary optical path 15, provided as an excitation channel, and the second secondary optical path 17 provided as a reflection channel are identical. With these beam splitters 7, 9, 11, 13 it is possible to take account of changes in the spectral range of an electromagnetic beam received.

A longer wave fluorescence 31 is transmitted by the first and second beam splitter 7, 9 and is uncoupled by the fourth beam splitter 13 into the fourth secondary optical path 19 provided as a fluorescence channel. The fourth beam splitter 13 is designed so that residual intensities of the excitation 27 are transmitted and only a desired spectral range of the fluorescence 31 is uncoupled from the main optical path 5.

Moreover, the fluorescence meter 1 has two sensors 33, 35. The first sensor 33 is arranged in the second secondary optical path 17 from the left, provided as a reflection channel, and is intended for detection of at least one spectral range of electromagnetic radiation, in this case reflection 29, emitted or reflected by the specimen 3. The second sensor 35 is arranged in the fourth secondary optical path 19, provided as a fluorescence channel, and is intended for the detection of at least one spectral range of the electromagnetic radiation emitted by the specimen 3, which is provided as fluorescence 31.

FIG. 2 shows a second embodiment of a fluorescence meter 37 which, like the fluorescence meter 1 shown in FIG. 1, comprises four beam splitters 7, 9, 11, 13, band-passes 21 and lenses 23 within the main optical path 5 and in this case four secondary optical paths 15, 17, 19, 39. The electromagnetic source 25 produces the excitation 27 indicated by the arrow, which is linked into the main optical path 5 by the first beam splitter 7 from the first secondary optical path 15 and reaches the specimen 3.

With the fluorescence meter 37 thus equipped, up to three fluorescences 41, 43, 45 are stimulated by the excitation 27 on or in the specimen 3 and corresponding radiation is emitted. The first beam splitter 7 links the shortwave excitation 27 into the main optical path 5. The three beam splitters 9, 11, 13 reflect the spectral ranges of the fluorescences 41, 43, 45 emanating from the specimen 3 or electromagnetic beams emitted by the specimen 3, which are to be detected by the sensors 33, 35, 48, out of the main optical path 5 into the secondary optical paths 17, 19, 39, so that they reach the sensors 33, 35, 47 provided there.

FIG. 3 shows a third embodiment of a fluorescence meter 47 with which two excitations 49, 51 can be provided by two electromagnetic sources 25, 55 arranged in different secondary optical paths 15, 39. With this fluorescence meter it is possible to detect up to two fluorescences 53, 54 of different wavelengths.

With the fluorescence meter 47 thus equipped, the specimen 3 is excited or acted upon by two excitations 49, 51 of different wavelengths, so that up to two fluorescences 53, 54 of different wavelengths are stimulated by the specimen 3. The excitations 49, 51 are produced by the electromagnetic sources 25, 55 and are linked into the main optical path 7 by the first and third beam splitters, 7, 11 from the left. The second and fourth beam splitters 9, 13 from the left reflect the spectral ranges of the fluorescences 53, 54 which are to be detected from the main optical path 7 into the secondary optical paths 17, 19, where detection takes place by means of the sensors 57, 59. Within the scope of a possible use, a first of the two excitations 49, 51 may be a positioning beam and a second of the excitations 49, 51 may be a measuring beam. It is envisaged that the positioning beam serves to position the measuring beam and/or the fluorescence meter 47.

There are other possibilities for equipping fluorescence meters 1, 37, 47 of this kind, providing at least one excitation with at least one wavelength and for detecting at least one fluorescence and/or reflection of various wavelengths. All three fluorescence meters 1, 37, 47 have confocal optical paths for the excitations 27, 49, 51 and electromagnetic beams emitted in front of the specimen 3, i.e. the fluorescences and reflections 29, 31, 41, 43, 45, 53, 54. The sources 25, 59 are usually light sources which mainly produce electromagnetic radiation in the visible range, i.e. light beams. It is also possible to produce radiation in the UV and NIR range.

Figure 4:
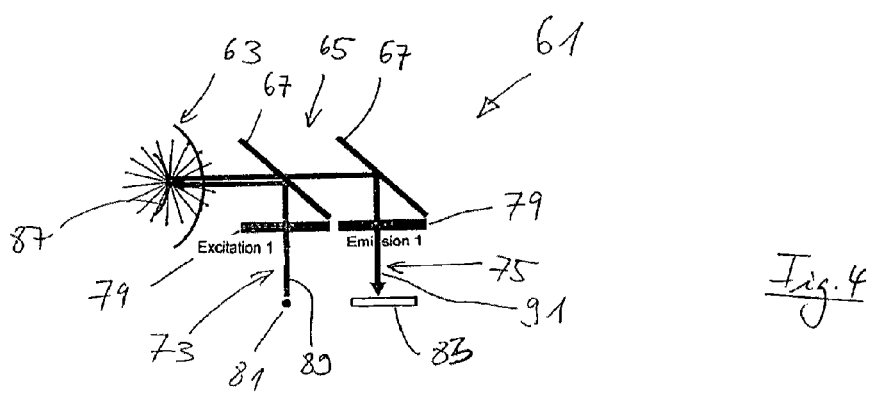
FIG. 4 shows a fourth embodiment of the fluorescence meter, shown schematically, for taking account of a positioning beam.
Figure 5:
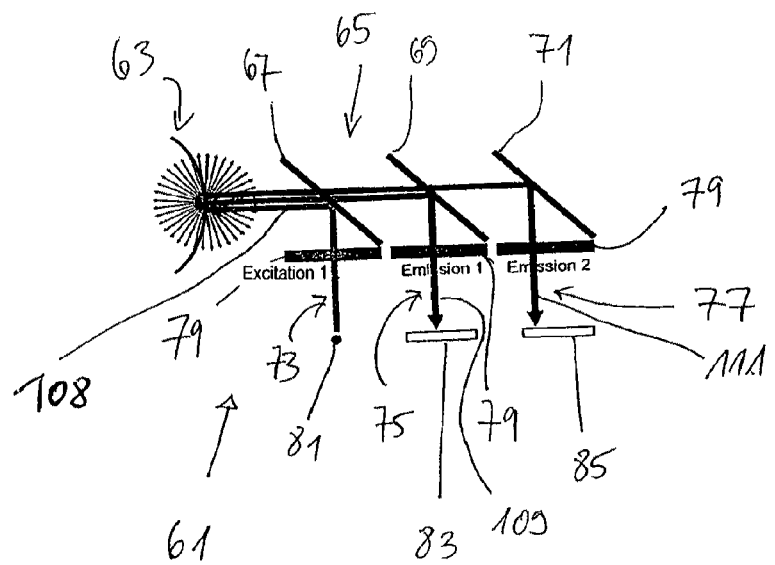
FIG. 5 shows the fluorescence meter shown in FIG. 4, taking account of a measuring beam.

FIGS. 4 and 5 show a fourth embodiment of a fluorescence meter 61 for examining an eye 63 for excitation and emission (fluorescence and reflection), this meter 61 also being provided with confocal optical paths for excitation and emission (fluorescence and reflection). It is suitable for providing a measuring beam 108 (FIG. 5) and a positioning beam 89 (FIG. 4) which are subject to various requirements. The fluorescence meter 61 has a main optical path 65 with beam splitters 67, 69, 71 arranged therein. Band-passes 79 are arranged in secondary optical paths 73, 75, 77. In the first secondary optical path 73 there is a source 81 and in the other two secondary optical paths 75, 77 there are sensors 83, 85. The third beam splitter from the left 71, the third band-pass from the left 79, the third secondary optical path 77 from the left and the second sensor 85 from the left are shown only in FIG. 5 while for clarity FIG. 4 does not show these components.

The positioning beam 89 which carried out the positioning of the measuring beam 108 using the inherent fluorescence of the lens 87 of the eye (FIG. 4) has only a short focal length. This implies a steep radiation or light cone which has a high resolution in the direction of the main optical path 65 and thus ensures precise depth positioning in front of the eye 63. The fluorescence meter 61 comprises a confocal system which ensures a common focal point of an excitation of the positioning beam 89 and of an excited inherent fluorescence 91 of the lens 87 of the eye. This ensures that only the excited inherent fluorescence 91 is detected and measured by the first sensor 83.

Figure 6A:
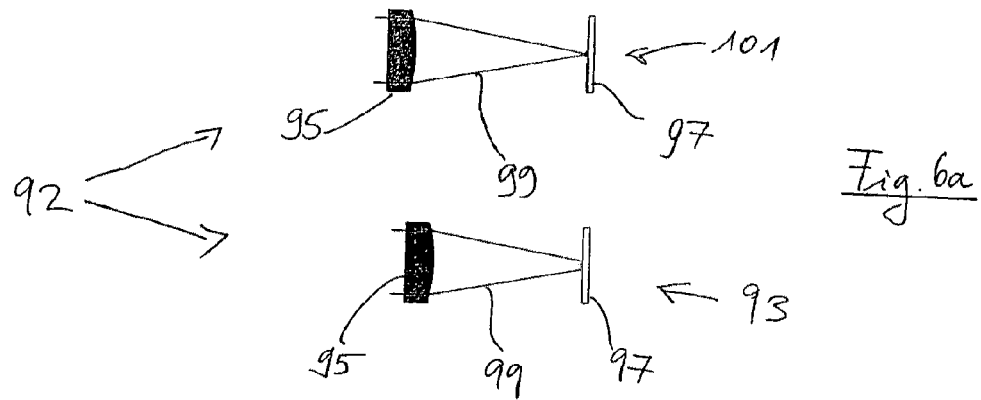
FIG. 6a shows a confocal system, shown schematically.

As an illustration, reference is hereby made to FIG. 6a which diagrammatically shows, by means of a first configuration 93 shown at the bottom, for a confocal system 92 with a lens 95 and an object 97, a positioning error in the focusing of an electromagnetic beam 99. The second configuration 101 shown at the top in FIG. 6a, on the other hand, shows the confocal system 92 with the lens 95, which is positioned at an optimum distance from the object 97 taking account of a wavelength of the electromagnetic beam 99. In this confocal system 92 the electromagnetic beam 99 is now focused precisely on the object 97, and the excitation and fluorescence have the same optical path.

Figure 6B:
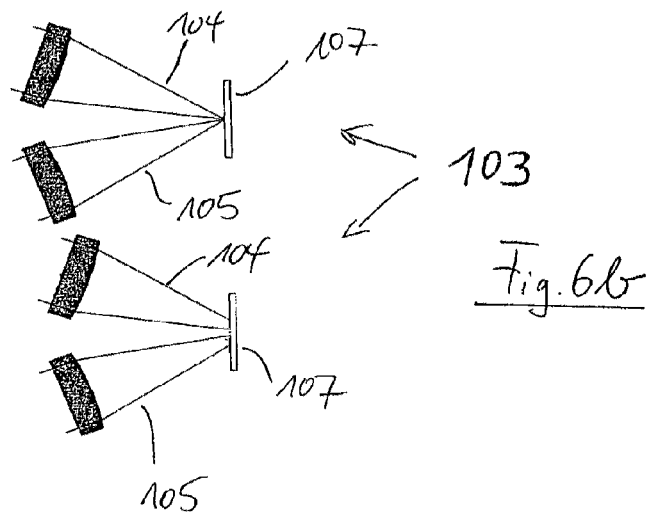
FIG. 6b shows a non-confocal system, shown schematically.

In the case of the measuring beam 108, which is excited by the electromagnetic source 81, this is reversed. Here, a longer focus would have less influence on a measuring signal in positional errors, which would in turn result in a greater, tolerance in positioning. However, at the same time a longer focal length also results in a smaller numerical aperture and hence less electromagnetic radiation received or less light received, proceeding from the excited fluorescence. This leads to lower sensitivity of the fluorescence meter 61. A compromise has to be reached here. Separate optical paths for the excitation and the detected emission, as are schematically shown by means of a non-confocal system 103 in FIG. 6b, cannot be used. If the focal point of the excitation 104 and fluorescence 105 do not coincide and the distance from the eye 63 does not match precisely, it is possible that any electromagnetic radiation received does not originate from the fluorescence 105 excited, and in this way the measurement is noticeably falsified.

This problem is solved with the confocal system inside the fluorescence meter 61 according to FIGS. 4 and 5. This reacts to positioning errors with a degree of tolerance.

Another advantage resulting from the confocal system is that by exciting the measuring beam 108 it is possible to detect emissions 109, 111 with two fluorescence wavelengths. If the different fluorescence wavelengths were measured at different locations, regional differences in concentration on the eye could lead to measuring errors. In the fluorescence meter 61 the two fluorescence wavelengths and the excitation wavelength have a common focal point on the cornea of the eye 63. The combined emissions 109, 111 can be spectrally broken down by the beam splitters 67, 69, 71 and detected by the sensors 83, 85.

In the fluorescence meter 61 the beam splitters 67, 69, 71 in the form of dichroic mirrors and the interference band-passes 79 are optimised to a certain angle. The interference band-passes 79 allow the beams to pass through at right-angles to their surface. In the beam splitters 67, 69, 71 or dichroic mirrors, slopes of 45° to the main optical path 65 are provided. The beam patterns in FIGS. 4 and 5 satisfy all these conditions if electromagnetic beams pass through the optical device in a collimated manner by means of lenses.

In the measuring beam 108 and the positioning beam 89, some of the electromagnetic radiation emitted or reflected by the eye 63 as an emission 75 has to pass through one or two of the dichroic mirrors 67, 69. These electromagnetic beams 89, 108 do not strike the surfaces of these dichroic mirrors 67, 69 in perpendicular manner but are broken up by them. After passing through a filter substrate of the dichroic mirrors 67, 69 they are broken back again. The beam offset thus produced is 0.26 mm for each dichroic mirror 67, 69 passed through. This is taken into account in the positioning of the dichroic mirrors 67, 69, 71 and the configuration of the optical paths 65, 73, 75, 77 of the fluorescence meter 61.

Numerous investigations of the eye 63 have shown that the positioning of the positioning beam 89 and of the measuring beam 108 is of great importance. One reason for this is the wide range of inherent fluorescences of the different regions of the eye 63. The design of the fluorescence meter 61 is based on the data of Gullstrand's eye, which represents a standard eye, derived from the measurement of a large number of human eyes. Relevant dimensions, radii and refractive indices of Gullstrans's eye are taken into account.

Figure 7A:
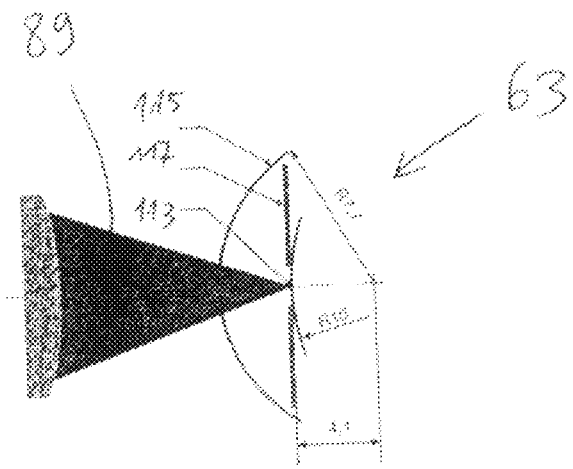
FIGS. 7a and 7b show details of the positioning of a positioning beam (FIG. 7a) and of a measuring beam (FIG. 7b) with respect to the fluorescence meter shown in FIGS. 4 and 5.
Figure 7B:
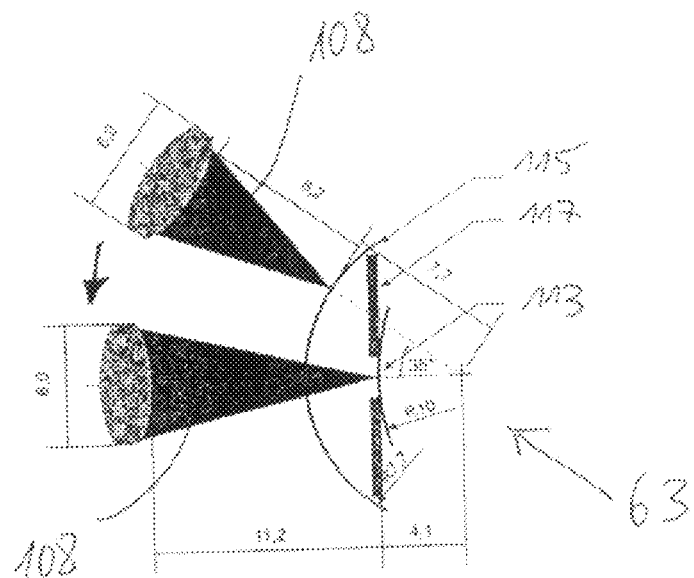

FIGS. 7a and 7b show details of the positioning of the positioning beam 89 and measuring beam 108, respectively, from FIGS. 4 and 5, the numbers representing distances and radii in millimeters. When carrying out an investigation of the eye 63 using the fluorescence meter 61 it is envisaged that the positioning beam 89 strikes the eye accurately (FIG. 7a). This ensures that the complete beam cone of this excitation produced by the positioning beam 89 passes through the pupil onto the lens 113 of the eye. This achieves maximum excitation and sensitivity.

The fluorescence meter 61 is moreover constructed so that a focal point of the measuring beam 108 is located on the cornea 115 and as positioning continues (arrow) lands on the iris 117 FIG. (7b). The substantially lesser inherent fluorescence of the iris 117 compared with the lens 113 of the eye 63 of the sclera is used, so that the measuring signal is falsified less. As with the positioning beam 89 a perpendicular incidence reduces the reflection.

Figures 8A, 8B:
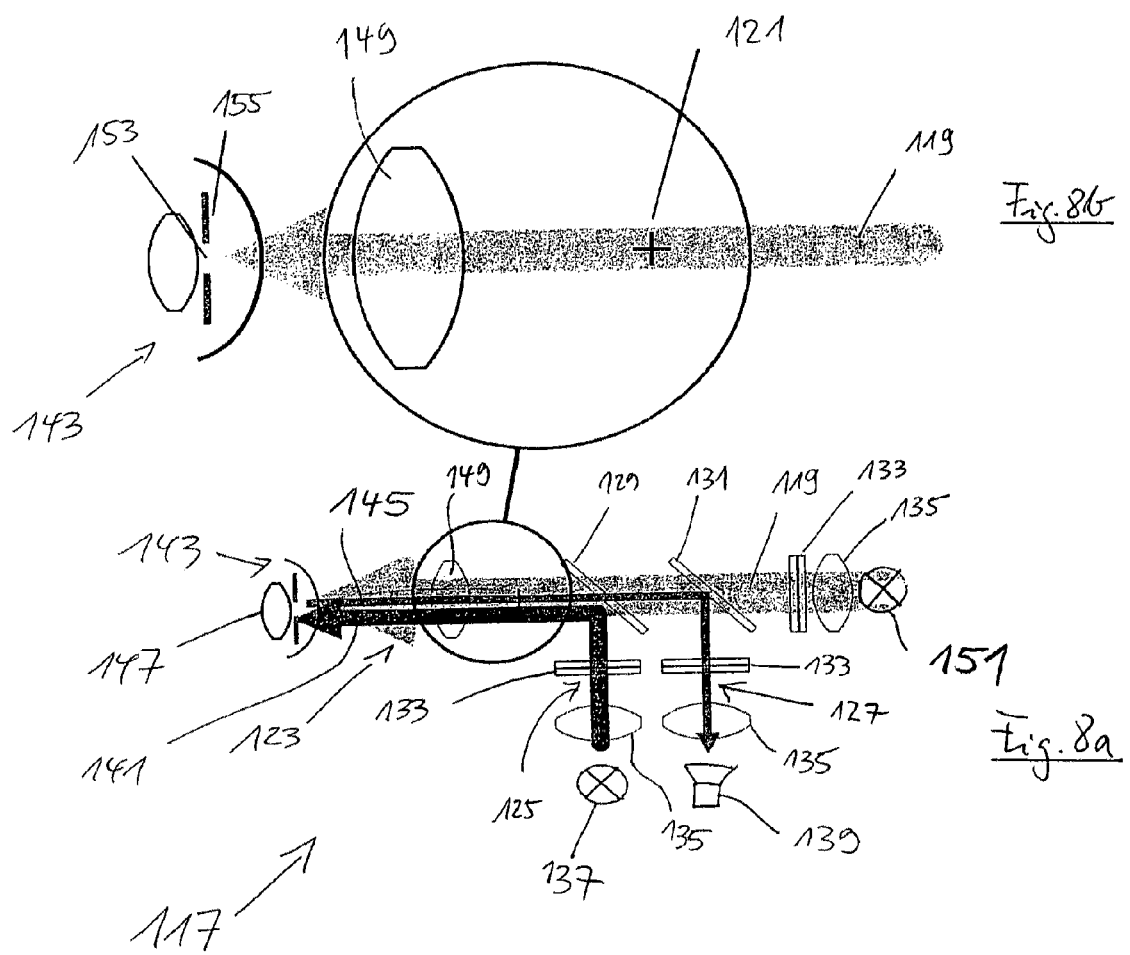

FIGS. 8a and 8b diagrammatically show a confocal fluorescence photometer or fluorescence meter 117 with background illumination (backlight) 119, which is produced by a lighting source 151, and a marking 121 or an orientation point (reticle) for better positioning of the fluorescence meter 117.

Similarly to the preceding Figures, the fluorescence meter 117 shown in FIG. 8a has a main optical path 123 and a first and a second secondary optical path 125, 127. FIG. 8b shows details of these on a larger scale. Moreover, this fluorescence meter 117 is equipped with beam splitters 129, 131, band-passes 133 and lenses 135. A source 137 for electromagnetic radiation or light, arranged in a first secondary optical path 125 from the left, is intended to provide excitation 141 of the eye 143. The inherent fluorescence 145 of the lens 147 of the eye is uncoupled from the main optical path 123 of the fluorescence meter 117 through the second beam splitter 131 from the left into the second secondary optical path 127 from the left and detected or picked up by the sensor 139 arranged there.

In this confocal fluorescence photometer or fluorescence meter 117, the excitation 141 is produced with an excitation wavelength and the inherent fluorescence 145 is detected with a fluorescence wavelength. By means of the marking 121 (reticle) located behind an exit lens 149, a user or patient has a target on which the can concentrate during the measurement or examination of his eye 143. In conjunction with the backlight 119, which is required on the one hand to illuminate the marking 121 (reticle) and on the other hand for contracting the pupil 153 through the iris 155, the use of thresholds makes it possible to achieve accurate positioning of the fluorescence meter 117 in front of the eye 143. The marking 121 is in the form of a cross in this example. The backlight 119 produced by the lighting source 151 shines only weakly, so that the eye 145 is not excessively irritated during the examination. An electromagnetic beam provided for the excitation 141 is produced only for a few milliseconds by the source 137 during the examination and is therefore barely detectable.

Figure 9:
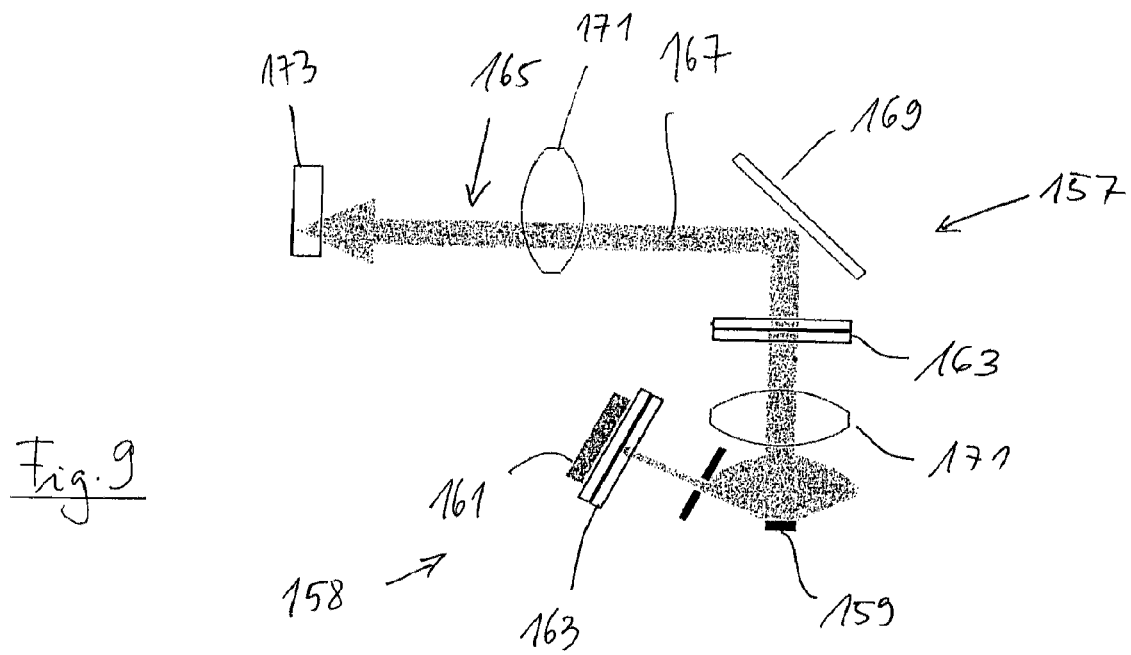
FIG. 9 shows a sixth embodiment of the fluorescence meter with a device for measuring an excitation output, shown schematically.

FIG. 9 schematically shows a device for measuring a radiant output of an electromagnetic source 159 of a fluorescence meter 157. For stabilising the radiant output, electromagnetic beams 167 emitted by the source 159 are continuously measured by a photodiode 161. In order to compensate the spectral shift by the changing temperature in front of the photo-diode or monitor diode 161 there is the same band-pass 163 as in an actual main optical path 165 for the excitation. The correction of the source 159 and hence of the radiant output takes place in real time.

This fluorescence meter 157 shown in FIG. 9 also has a beam splitter 169 and lenses 171. The excitation 167 produced by the source 159 is deflected by the beam splitter 169 into the main optical path 165 and thus reaches a specimen 173 which is to be examined. As the same optical devices, particularly the same band-passes 163, are arranged in the optical path between the source 159 and the specimen 173 and between the source 159 and the photodiode 161, it is ensured that in the photodiode 161 electromagnetic beams are received with the same radiant output as on the specimen 173, so that he radiant output can be accurately determined and the source 159 can thus be stabilised.

Because of its anatomical and physiological peculiarities the eye lends itself particularly to the use of optical diagnostic and therapeutic methods. The first attempts to cure specific eye diseases using focused beams of light go back to the 1950s. At that time it was shown that focused sunlight could be used as an operating instrument.

With the fluorescence meters proposed here, laser-assisted applications based on photometric and photomechanical effects are also possible, for example, if the sources of the fluorescence meters are correspondingly constructed as lasers. Diagnostic methods for investigation using the fluorescence meters make use of the various reflection characteristics of the objects to be examined, particularly eyes. Examples of these are measurements of retinal layer thicknesses of nerve fibres by detecting the polarisation state (measurement of the Stokes vector) or coherence-optical measuring systems for determining intraocular distances (optical coherence tomography, OCT).

The spectral characteristics of the electromagnetic radiation emitted by the tissue of the eye provides information as to the concentrations of individual substances involved in metabolism of the eye. Substance-specific fluorescences are measured with miniature optical devices using the fluorescence meters described here.

The optical device of the present fluorescence meters is small compared with the optical devices of known fluorescence meters, while its functionality is increased and improved. Known fluorimeters are of a size such that only one diagnostic beam can be used per eye.

Figure 10:
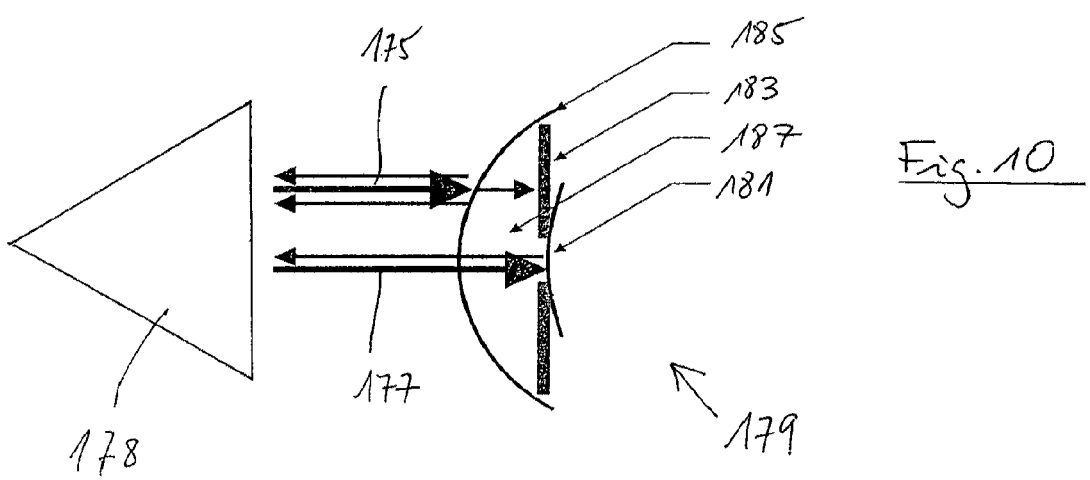
FIG. 10 shows a seventh embodiment of a fluorescence meter, shown schematically.

A fluorescence meter 178 diagrammatically shown in FIG. 10, on the other hand, is so small that two separate beams 175, 177 produced by this fluorescence meter 178 can be measured simultaneously on one eye 179. One of the two beams serves as a measuring beam 175 which reads out the desired information, while the other acts as a positioning aid (positioning beam 177).

The positioning is carried out with the aid of different strengths of inherent fluorescence of the various tissues substances in the eye 179. Investigations show that the lens 181 of the eye, with suitable optical excitation, has roughly a hundred times higher fluorescence intensity than the adjacent iris 183. Using a minimum intensity threshold of the positioning beam 177 it is possible to determine when the measuring beam 175 is ideally aligned and can be measured.

Ideally in this case means that the measuring beam 175 should be focused on the cornea 185 of the eye 179 such that the measuring beam 175 as it continues reaches the iris 183. This reduces unwanted background fluorescence to a minimum as the iris 183 fluoresces in the relevant spectrum less than the sclera or the lens 181 of the eye behind the anterior chamber 187 of the eye 179.

The measuring beam 175 excites the substances which are to be detected in the eye 179 at a wavelength of for example 465 nm. The optical device, not shown in FIG. 10, of the schematically shown fluorescence meter 178, which is of similar construction to the fluorescence meters shown in the previous Figures, has a common main optical path for electromagnetic beams produced during an examination. This main optical path is in the centre of an optical cylinder.

The secondary optical paths run perpendicularly to the main optical path and are linked and uncoupled with dichroic mirrors rotated through 45° in each case. With this construction it is possible to use the optical path, for example the main optical path, for excitation simultaneously in the opposite direction to the receiving of the fluorescence, so that once again a confocal system is obtained The fluorescence wavelengths of the measuring beam are 520 nm and 590 nm, for example. They are received jointly within the fluorescence meter 178 and are then spectrally broken down and measured using the dichroic mirrors and interference band-passes. Details of this are shown in the proceeding Figures.

The main optical path is arranged substantially centrally in the optical device of the fluorescence meter 178. Electromagnetic excitation beams are coupled into the main optical path again using dichroic mirrors and focused on the lens 181 of the eye. The inherent fluorescence of the lens 181 excited, e.g. 520 nm, is collimated into the main optical paths and uncoupled into one of the secondary optical paths by means of two dichroic mirrors. For better spectral separation, interference band-passes are again used. With the positioning beam 177 only one fluorescence wavelength is measured.

The electromagnetic beams or the light for excitation yields a source constructed as an LED lamp. This LED lamp emits within the desired spectrum and has a very high output.

FIGS. 11a, 11b, 11c, 11d show another embodiment of a fluorescence meter 189 in schematic view with a main optical path 191 and three secondary optical paths 193, 195, 197, while in the two first secondary optical paths 193, 195, viewed from the left, in addition to optical modules such as band-passes 199 and lenses, sensors 201 are provided for detecting electromagnetic beams received. In the third secondary optical path 197, in addition to an electromagnetic source 203, other optical devices are provided such as at least one lens 200 and a band-pass 199. In the main optical path 191, besides the beam splitters 205, 207, 209, a condenser lens 211 is provided. Using the fluorescence meter 189 it is possible for example to carry out examination of an eye 213.

In the manufacture of the fluorescence meter 189, CAD data of a design are used as the geometric basis for simulation. They thus correspond exactly to those of the fluorescence meter 189 produced later. In the optical device of the fluorescence meter 189, the electromagnetic radiation of the excitation 201 is collimated and radiated through two interference band-passes 199. As a result of the change in the coupling into the main optical path 191, only one dichroic mirror 211 is provided for this purpose. Focusing on the cornea of the eye 213 is taken over by a condenser lens 211. The fluorescences 215, 217 excited take the opposite pathway, being transmitted through a collimator lens and the first dichroic mirror 205. On the second dichroic mirror 207, again the spectral separation of the electromagnetic radiation emitted takes place. Fluorescence 215 with a shorter wavelength of 520 nm is uncoupled from the main optical path 111 at an angle of 90° and after passing through two interference band-passes 199 it is focused on the sensor 201. A longer wave part of the fluorescence 217 with a wavelength of 590 nm is transmitted and is deflected by a dichroic mirror 205 onto the interference band-passes that follow the main optical path 191. This is followed by focusing on the sensor 201.

Figure 11A:
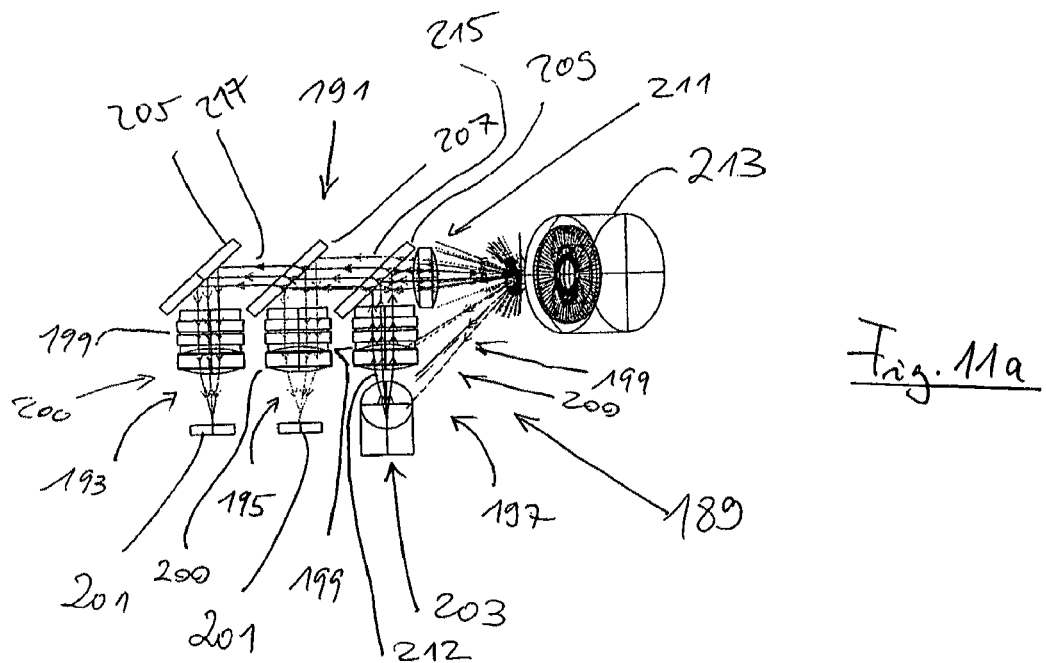
FIG. 11 shows an eighth embodiment of the fluorescence meter shown schematically, wherein in FIGS. 1b, 11c and 11d, optical paths of individual magnetic beams provided for measurement are shown separately.
Figure 11B:
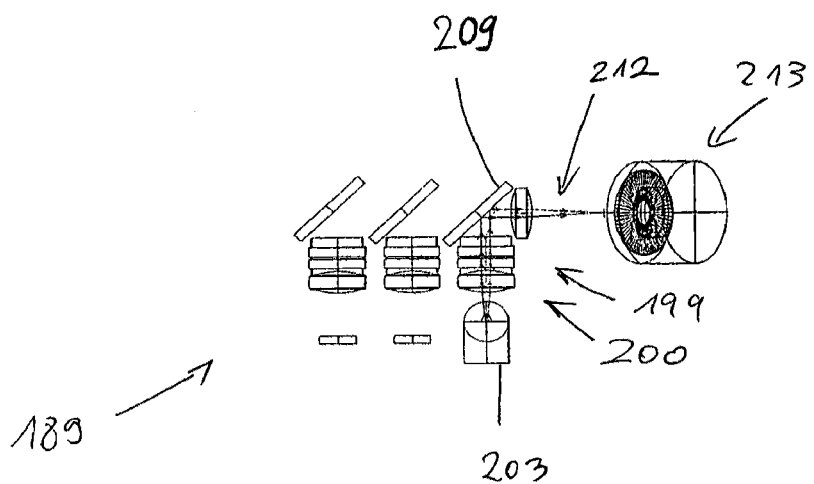
Figure 11C:
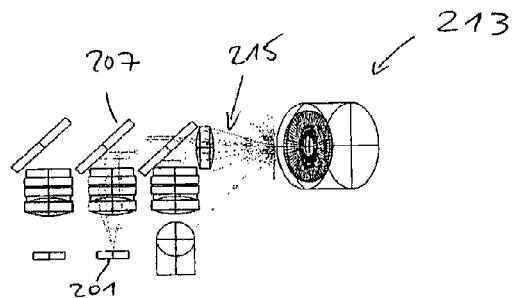
Figure 11D:
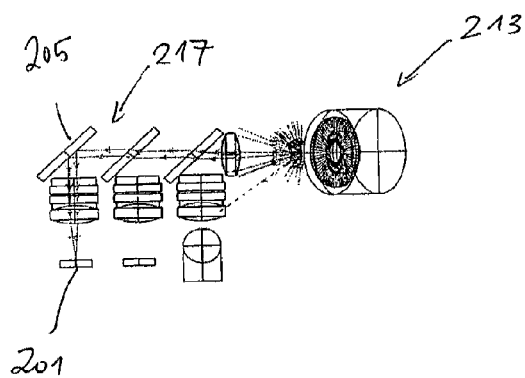

FIGS. 11b, 11c, 11d each show the fluorescence meter 189 illustrated in FIG. 11a, each one of these three Figures showing only one of the electromagnetic beams 212, 215, 217 used for examining the eye 213.

FIG. 11b shows the optical path for the excitation 212.

Figure 12A:
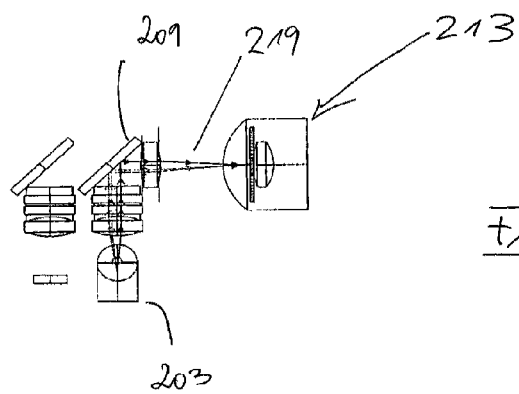
FIG. 12 shows a positioning beam (FIG. 12 a) for the fluorescence meter shown in FIG. 11 and an excitation (FIG. 12b) of this positioning beam for the fluorescence meter shown in FIG. 11.
Figure 12B:
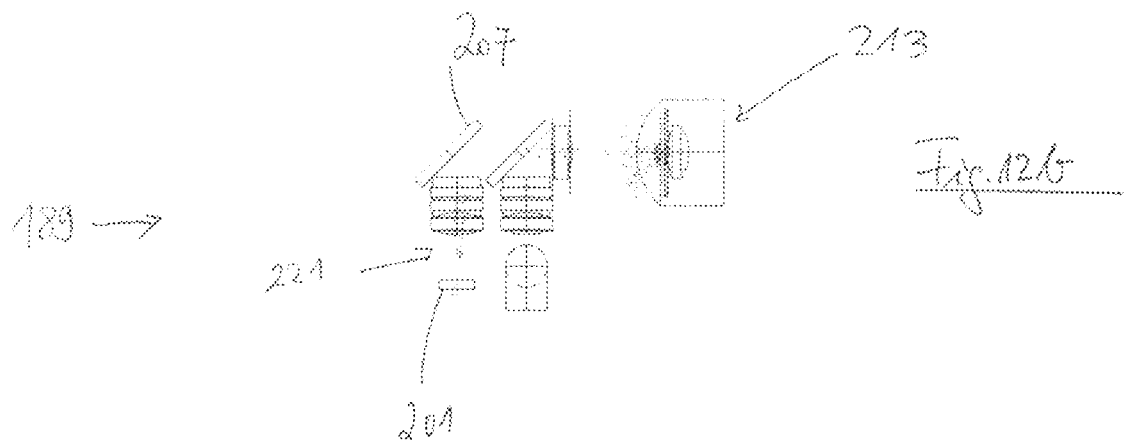

FIGS. 12a and 12b show the behaviour of a positioning beam 219 and an associated reflected excitation 221 of the positioning beam 219. An optical path of the reflected excitation 221 for the positioning beam 219 is shown in FIG. 12b.

With the fluorescence meter 189 it is possible to achieve high flexibility. This means that there is an extremely wide range of options for fitting lenses, shutters, filters and sources for providing the excitation 212, 219 for the measuring or positioning beam.

An optical device of the measuring beam 212 is compatible with that of the positioning beam 219. A design for the measuring beam 212 automatically meets the requirements of the positioning beam 219. Different focal lengths for the exit lenses are not specified.

The lenses used may be conventional standard lenses. Small sized Fresnel lenses may also be used. With plastic lenses there is the risk of inherent fluorescence. Possible sources of error must be eliminated with glass lenses. As this is not necessarily a system which provides an exact image, monochromatic and chromatic errors may be tolerated within limits. Consequently it is possible to use uncorrected lenses, namely spherical standard lenses.

Figure 13:
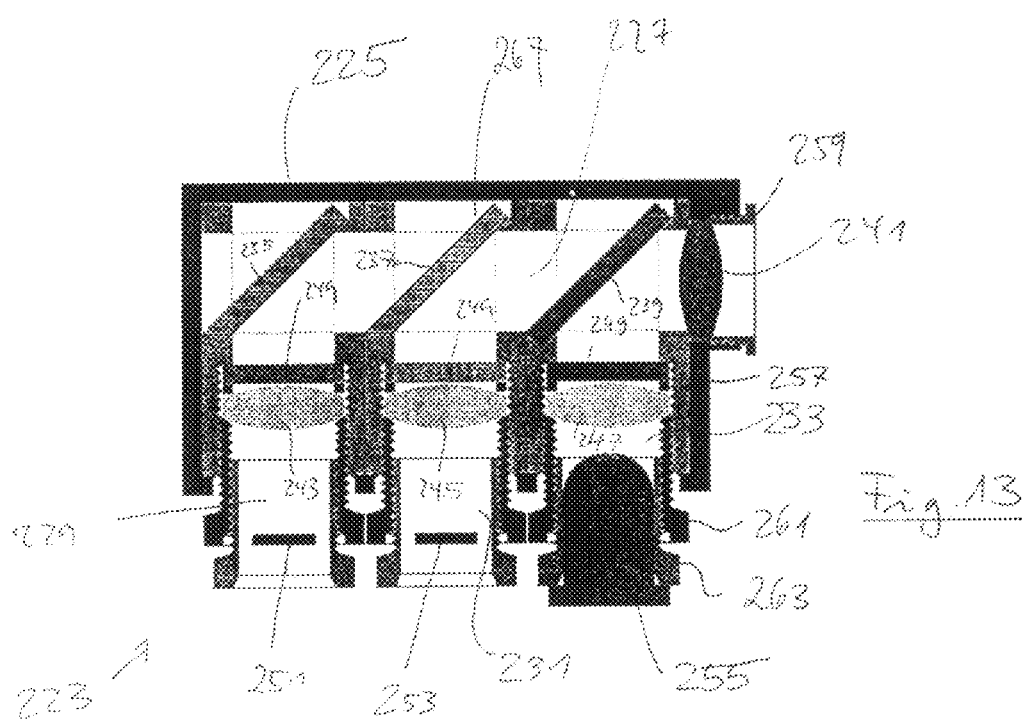
FIG. 13 shows an eighth embodiment of the fluorescence meter, shown schematically.

FIG. 13 diagrammatically shows a fluorescence meter 223 with a housing 225 which is CNC-milled from aluminium. Inside the housing 225 are provided a main channel 227 for a main optical path and, branching off it at an angle of 90°, secondary channels 229, 231, 233 for secondary optical paths. Inside the housing 225 are provided beam splitters 235, 237, 239 constructed as dichroic mirrors, lenses 241, 243, 245, 247, interference band-passes 249, sensors 251, 253 and a source 255 for electromagnetic beams.

Variable positioning of the lenses 241, 243, 245, 247, shutters and filters with a diameter of about 6 mm is achieved by means of screw-in sleeves 257, 259, 261, 263 in the housing 225. The exact placing of the source 255 and sensors 251, 255 in the focal point is carried out with a second sleeve 263, which is screwed into an internal thread of the first sleeve 261. The dichroic mirrors 235, 237, 239 are positioned precisely through recesses 267 inside the main channel 227. This fluorescence meter 223 may be of modular construction and provides the maximum flexibility with regard to equipping it with the optical elements envisaged.

The housing of the fluorescence meter can be produced without any major design changes by injection moulding and hence by mass production. A housing of this kind is produced for example by a stereolithographic process.

In this process of so-called Rapid Prototyping a desired shape for the half-shell of the housing is formed from a liquid polymer layer by layer using focused laser beams. At a focal point the laser intensity is high enough to effect polymerisation, i.e. the liquid polymer cures at this point. If a layer is scribed it is lowered so that it is again coated with a thin liquid polymer film. This can then be structured again. The resolution of the stereolithography is about 100 µm. For curing, the housing thus obtained in placed in a UV oven. Here, the polymerisation of the stereolithography product is completed.

The stereolithography product is multiplied using a vacuum casting method. The casting mould is produced from a silicon cast of the stereolithography product. The silicon mould can be used to cast between 15 and 30 components, the material properties of which correspond to those of the mass produced injection moulded part which would be obtained later.

The two half-shells for the housing are preferably provided with notches which can serve to accommodate lenses, filters, shutters and dichroic mirrors. To ensure that no ambient light penetrates from outside or transfers between the individual channels, a double light trap is incorporated. Two half-shells are held together by eyelets for snap-fit closures. Two semi-cylindrical webs for each half-shell serve to position an electronic plate and additionally secure the two half-shells.

The system shown in FIG. 13 for the fluorescence meter 223 is admittedly more flexible, as it permits smooth positioning of the optical components or elements, but it is more complex to produce and is not suited for mass production. Therefore, a fluorescence meter which is directly suitable for mass production is preferable. The position of the lenses and filters is laid down beforehand but it is possible to vary the positioning of the LED as the source for electromagnetic beams or light and the sensors.

The half-shell of the prototype has a high fidelity of details, A web and the notch of the light trap between the channels are cleanly formed. Eyelets of the snap-fit closure are recognisably moulded on.

Figure 14:
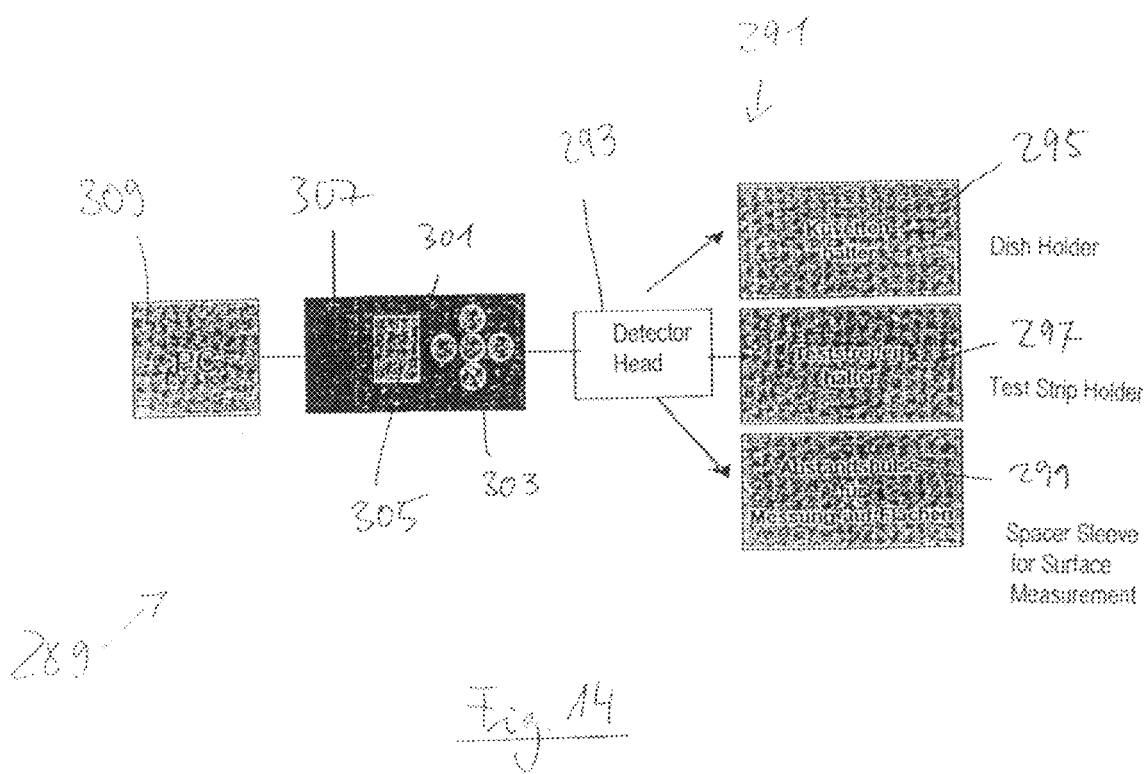
FIG. 14 schematically shows a preferred embodiment of an apparatus.

FIG. 14 diagrammatically shows an apparatus 289 having specimen holder 291 which is constructed so as to receive a use-specific optical detector head 293 or a fluorescence meter as shown in the preceding Figures. This specimen holder 291 has a dish holder 295 for receiving a specimen, a test strip holder 297 and a spacer sleeve 299 for surface measurement. The specimen holder 291 is moreover connected to a manual meter 301 schematically shown in FIG. 14, which has a keyboard 303 and a display 305. The manual meter 301 is connected to a computer 309 via an interface 307 or docking station. Using the manual meter 301 it is possible to control and carry out the measurement of a specimen with the detector head 293 in computer-aided and/or automated manner as well. It is also possible to regulate or control such a measurement with the computer 309. Evaluation of the measurement can be done using the manual meter 301 and/or the computer 309.

In contrast to known devices for optical investigation in which a specimen holder is mounted in a meter, with the apparatus 289 shown in FIG. 14 a meter, i.e. the detector head 293, or one of the fluorescence meters described hereinbefore is received in the specimen holder 291. The specimen holder 291 is of modular construction and, depending on the nature of the specimen to be examined, can be exchangeably equipped with a suitable detector head 293 or fluorescence meter to provide an electromagnetic excitation of a suitable wavelength. In addition, the specimen holder 291 is equipped with an x y z positioning unit with which it is possible to position the detector head 293 or fluorescence meter and the specimen in up to three spatial directions relative to one another and thus achieve suitable setting for carrying out the examination.

Thanks to the modular construction of the specimen holder 291 it is possible for a detector head 293 placed therein or connected thereto to be automatically recognised. Calibration data, compensating curves, concentration curves and the like suitable for carrying out and evaluating the investigation are stored in the detector head 293 or in a corresponding fluorescence meter and after transfer from the manual meter 301 these data are read out and used for computation. For the interface 307 with the computer 309 it is also optionally possible to carry out remote control of the examination and offline processing of data which have been stored during the examination by the manual meter 301. The data obtained with the apparatus 289 or with the detector head 293 may also, for example, be used to control or regulate technical equipment, e.g. in a production process. Communication with technical equipment of this kind is possible via the interface 307 or computer 309, taking account of these data.

Figure 15:
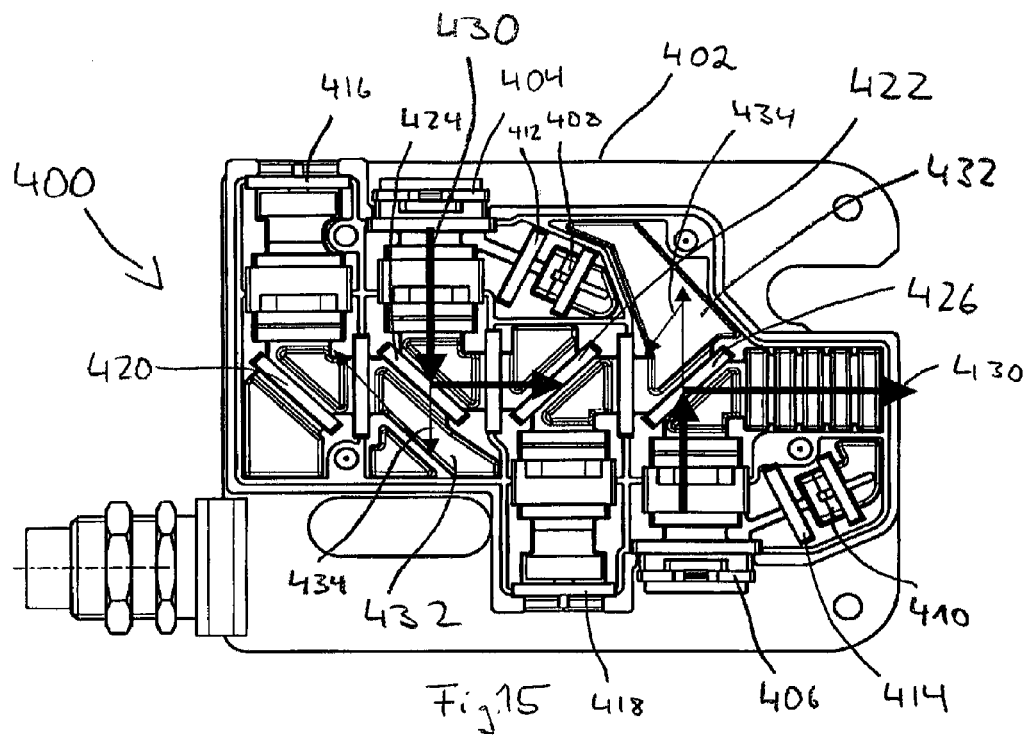
FIGS. 15 to 17 show another embodiment of the meter according to the invention in plan view.

FIG. 15 shows a possible embodiment of the meter according to the invention, generally designated 400.

It will be seen that all the components are integrated in a housing 402. A first source 404 and a second source 406 are provided, the first source 404 being associated with a first monitor diode 408 and the second source 404 being associated with a second monitor diode 410.

Between the first source 404 and first monitor diode 408 an optical module is provided, namely a first filter (beam splitter) 412. Similarly, a second filter 414 is arranged between the second source 404 and the second monitor diode 408.

Also shown are a first detector 416 and a second detector 418, which detect beams reflected through associated beam splitters 420 and 422. The first filter 412 and the second filter 414 correspond in their optical properties to a first beam splitter 424 and another second beam splitter 426, so that the monitor diodes 408 and 410 detect matching beams.

Arrows 430 indicate the optical paths of the beams produced by the meter, while light traps 432 substantially reduce the amount of scattered light, thus making it possible to obtain very good measurements.

Thanks to the specially developed housing shape with the integrated light traps 432, direct access of scattered light to the detector channel and hence to the detectors 416 and 418 is only possible after multiple reflections, for geometric reasons. The radiant energy meanwhile falls to an insignificant level and does not interfere with the measurement. The remaining fraction which is not coupled out by the beam splitters 424 and 426 is absorbed by the light traps 432 (arrows 434).

Figure 16:
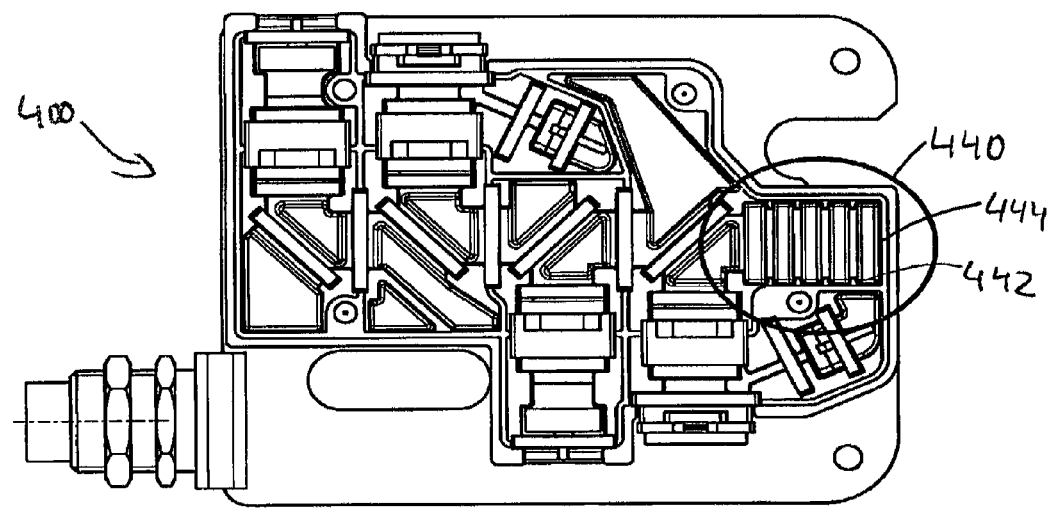

In FIG. 16 the region of the exit opening is shown inside a border 440. In this region additional light traps 442 are incorporated in the form of ribs. These reduce the scattered light which enters the system from outside through an entry lens 444. In addition, further filters which block unwanted spectral ranges may be inserted between the ribs or in the recesses formed by the ribs.

Figure 17:
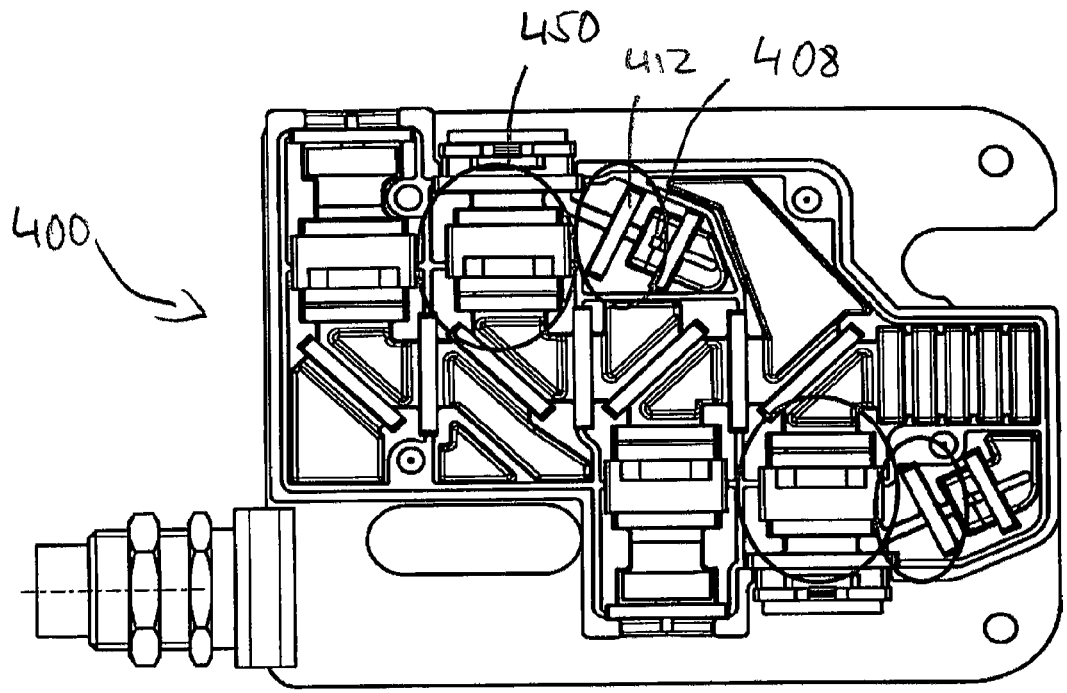

FIG. 17 shows the monitoring of the sources 404 and 406. For the monitoring and the subsequent regulation of the light output, the same filter 412 is installed in front of the monitor diode 408 as in the main optical path 450. The advantage of this is that a change in the light output possible caused by the spectral drift can be adjusted afterwards. The position of the monitor diode 408 is selected so that light influences penetrating the light sensor from outside do not have a disruptive effect on the regulation.

Figure 18:
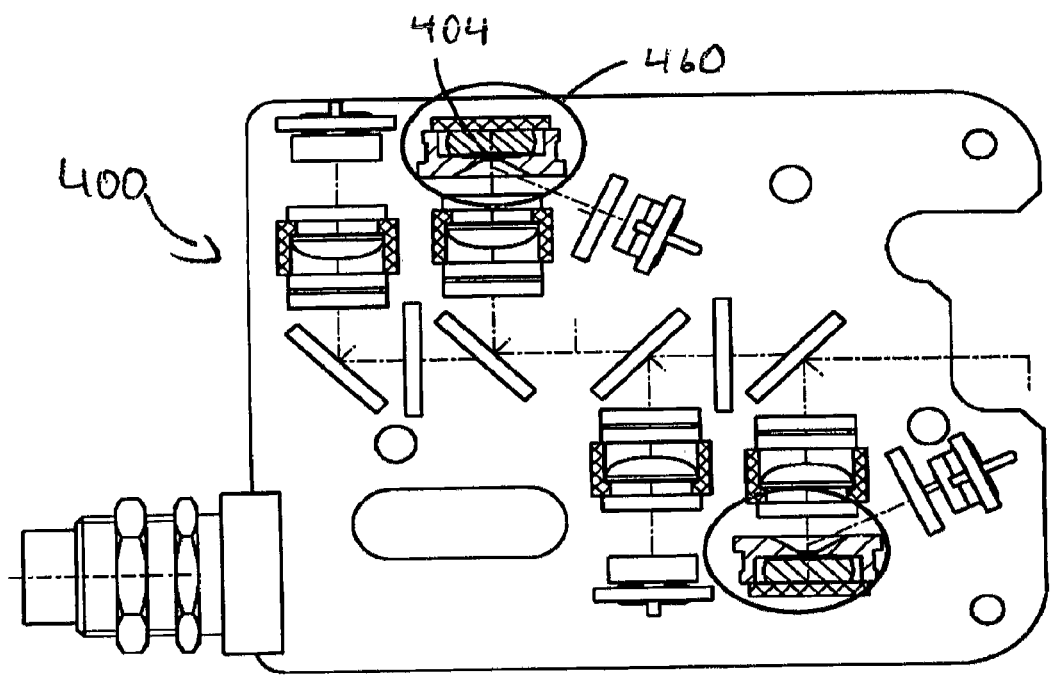
FIG. 18 shows the meter of FIGS. 15 to 17 in simplified view.

FIG. 18 illustrates the cooling of the sources 404 and 406. A cooling member 460 which surrounds the source 404 in constructed so that it makes the insertion of a shutter in front of the light source 404 superfluous and at the same time takes over the alignment of the excitation light source 404 in the housing. For this purpose the cooling member 460 has an opening.

Figure 19:
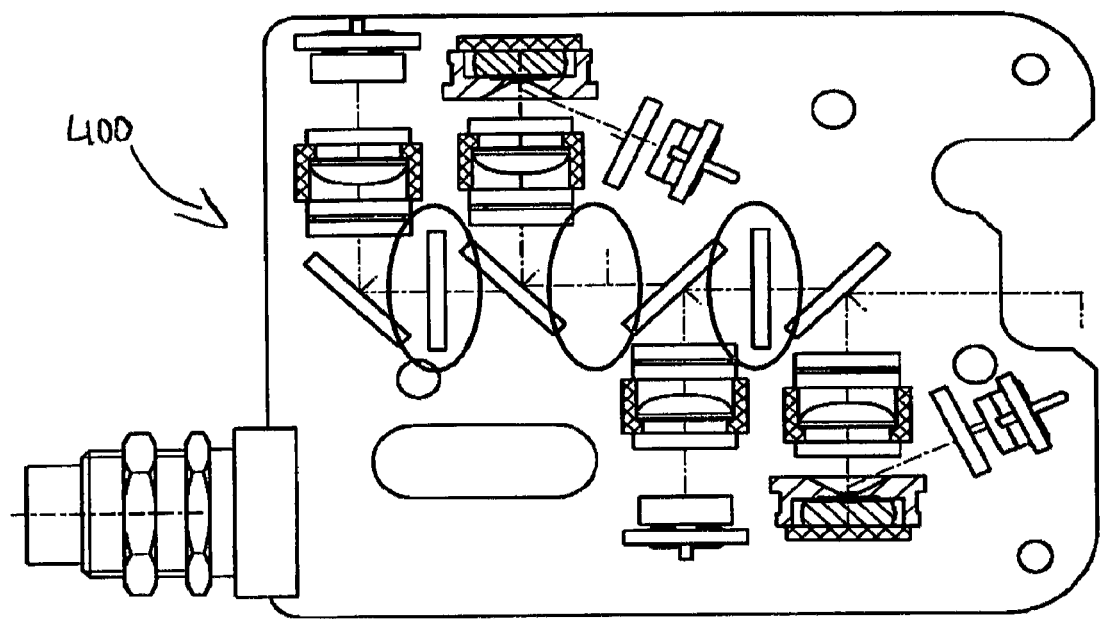
FIG. 19 shows the meter from FIGS. 15 to 17 in simplified view.

FIG. 19 shows the reduction in the crosstalk between excitation and emission. Thanks to the use of the imaging optics with a very long focal tube a low depth of focus has been obtained. This makes positioning easier. It is therefore now possible to carry out measurements very easily on surfaces or on specimens with a very high optical density. In off-axis systems specimens of this kind have to be positioned exactly or very highly diluted, which always involves serious errors and makes the reproducibility of the measurements poorer.

Figure 20:
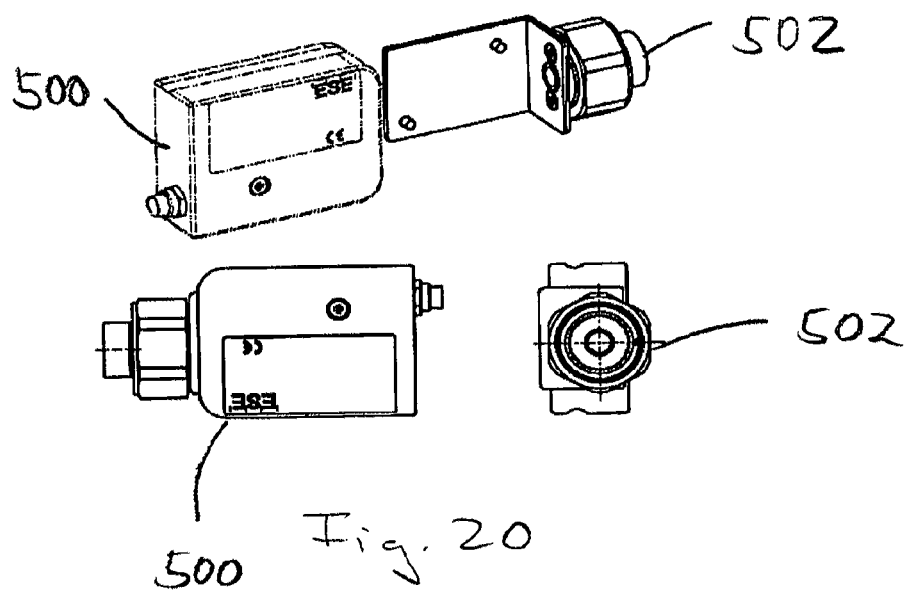
FIG. 20 shows a possible use of the meter according to the invention.

FIG. 20 shows a meter 500 or a sensor with a receptacle 502 or an adaptor. The sensor 500 is screwed onto the receptacle 502 without a front lens. The receptacle 502 contains the front lens which would otherwise be mounted directly on the sensor 500. Thus the focus is advanced into the flow of the medium which is to be measured. The receptacle 502 has a standard 1-inch connection and can thus be connected to a line. A ballcock is particularly suitable for this, as it can close off the line simultaneously in front of and behind the sensor 502. Thus, maintenance work such as cleaning or replacing the measuring window, for example, is made easier.

Figure 21:
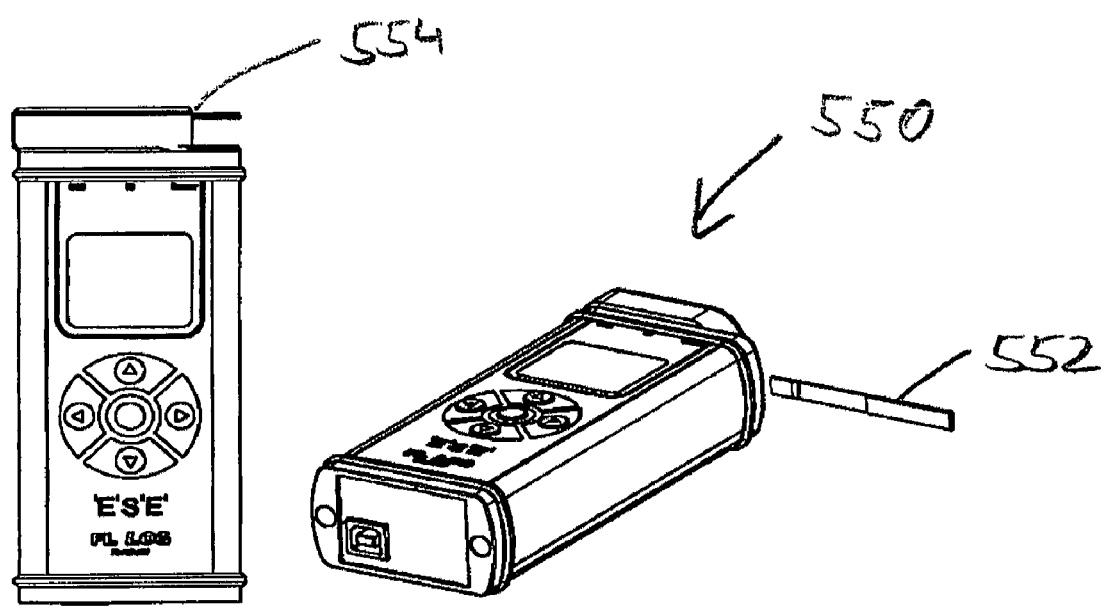

FIG. 21 shows another embodiment of the meter according to the invention in an operating unit 550. Here, a test strip 552 is placed directly in a receptacle 554. The sensor is located in the operating unit 550. The test strip 552 is inserted manually and pulled out during the measurement. The measuring window is determined by two light barriers. As there is relatively large distance tolerance in the sensor the guiding of the test strip 552 is designed to be relatively simple. The measurement is only recognised when the removal of the strip has taken place within a specified time window.

Figure 22:
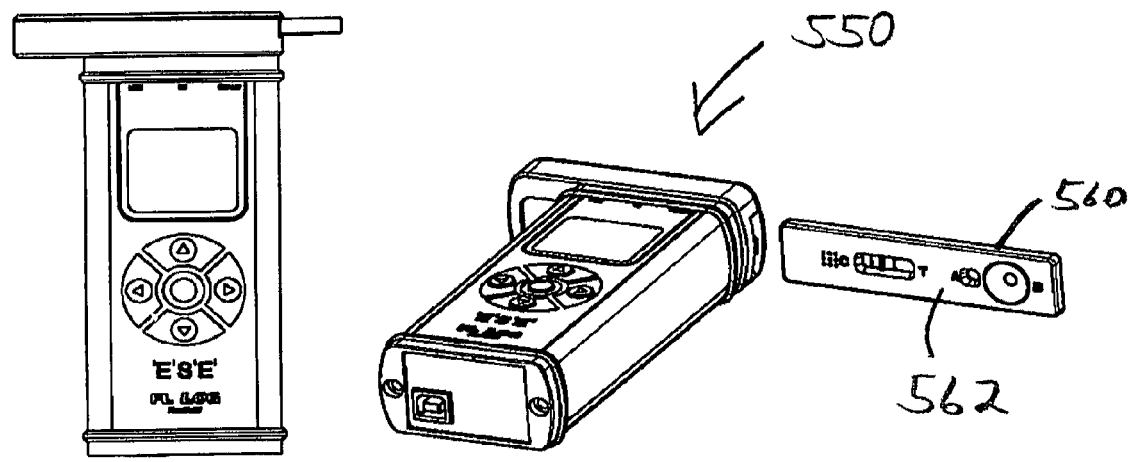

FIG. 22 shows a comparable arrangement with an operating unit 550. In this case a test strip 560 is located in a cassette 562. This cassette 562 has very high tolerances. As there is a large tolerance window for the positioning of the specimen the test strip 560 can very easily be measured in the cassette 562.

Figure 23:
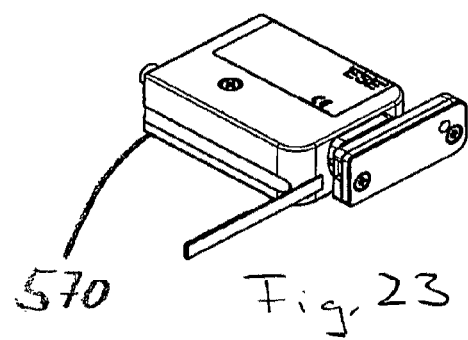

FIG. 23 shows that the strip reader is to be adapted to an external sensor 570.

FIG. 24 shows two embodiments 600 and 602 for surface measurements. By means of the confocal optics with a low depth of focus, fluorescent phenomena on the surfaces can be measured with ambient light. The first embodiment 600 has a guide 604 for microscope slides. The second embodiment 602 has a mechanical x y z guide 606.

Figure 25:
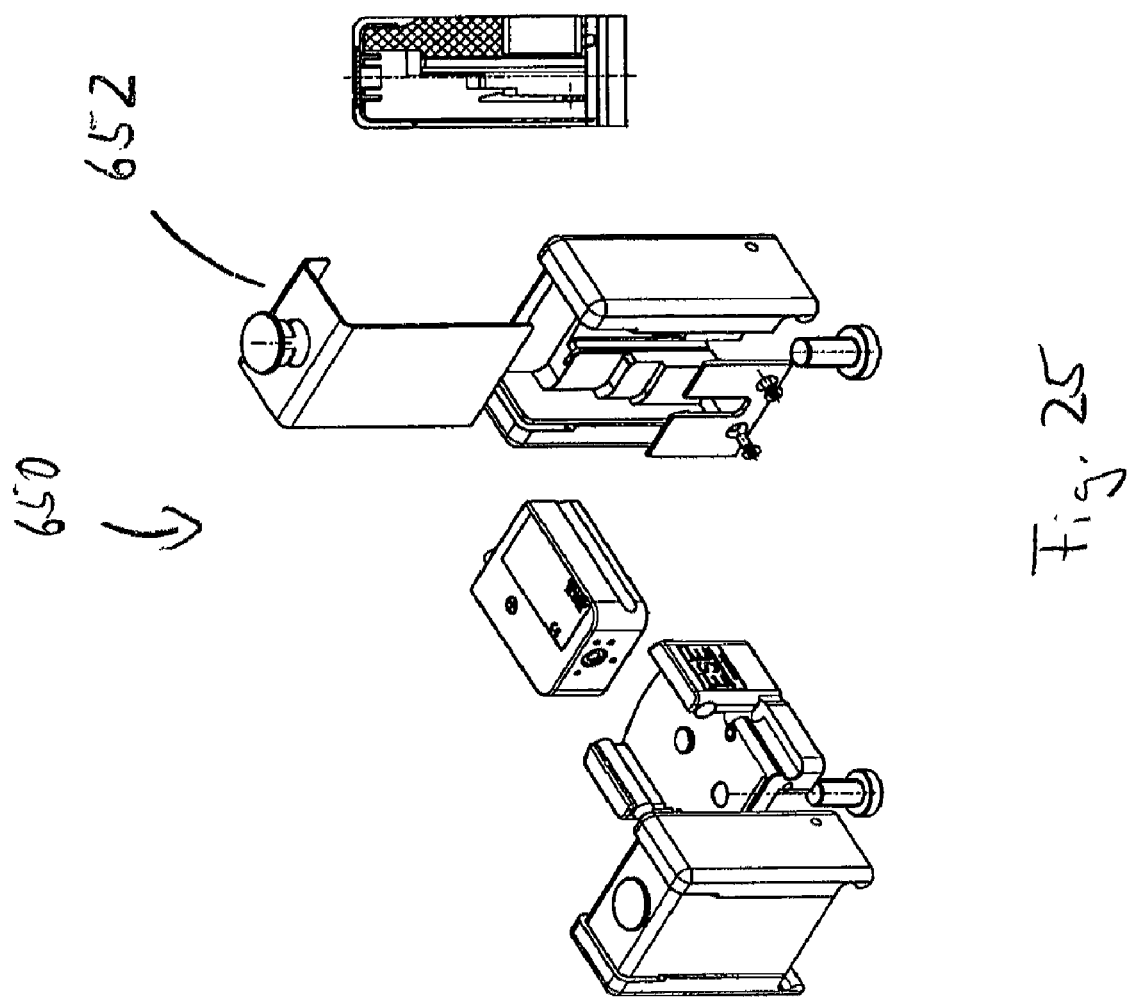

FIG. 25 shows an adaptor 650 in which both dishes of different constructions (throughflow, macro, micro, etc.) and also microscope slides or similar, including non-transparent specimens and specimen holders can be measured. A cover 652 has throughflow dishes through a separate passage for hose connections. The position of the dishes can be adjusted vertically. As with the PCR tubes it is also possible to connect the dish holder to the evaluating unit.

Figure 26:
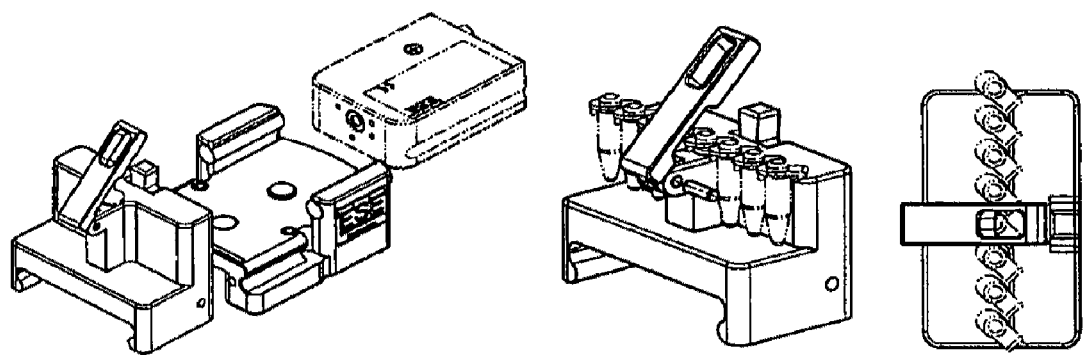
Figure 27:
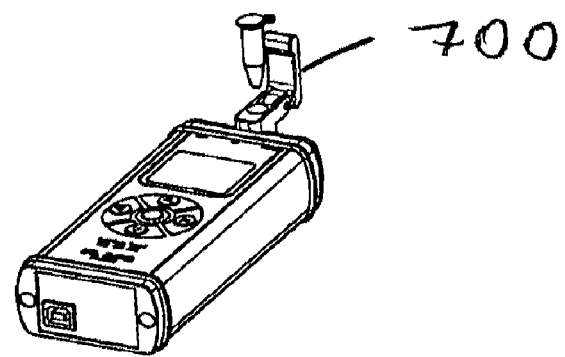

FIGS. 26 and 27 show that thanks to the design of the sensor it is possible for the first time to measure high resolution fluorescence in PCR tubes. Both individual tubes and whole strings of tubes can be measured. This can be done with 0.5 ml and with 0.2 ml PCR tubes. Thus, FIG. 27 shows a sensor which is integrated in the evaluating unit. A PCR tube adaptor 700 is mounted directly on the evaluating unit.

The invention as illustrated in the preceding Figures provides a miniaturised fluorescence meter with increased functionality. The measuring principle used makes use of the property of biological substances to emit light in a substance-specific spectrum when suitably excited. Excitation energy is supplied in the form of a focused electromagnetic light beam or laser beam. The system operates with two optical modules, one of which is used for positioning while the other is used for the actual measurement. One variable of these optical modules enables both of them to detect fluorescence simultaneously in one eye. All the fluorescence meters are of confocal construction, meaning that at least one electromagnetic beam for exciting the specimen and at least one electromagnetic beam for the fluorescence and/or reflection of the specimen at least partly share an optical path, in this case the main optical path.

LED lamps for providing the excitation energy are normally packaged in a transparent epoxide housing which has three functions. It protects an LED from environmental influences, ensures additional discharge of heat and collimates light or electromagnetic radiation emitted by the LED.

In the search for a suitable LED lamp as the source of electromagnetic radiation in the fluorescence meter it was found that LED lamps which have a lens-shaped housing, with an epoxide housing, have radiation characteristics which are not suitable for the fluorescence meter which is to be provided. Thus with conventional LED lamps, for example, it is not possible to focus on a lens inside one of the optical paths of the fluorescence meter. Only in this way is it possible to achieve optimum focusing of an electromagnetic beam produced by the LED lamp on a lens within one of the optical paths of the fluorescence meter. Alternatively, it is possible to choose, for the fluorescence meter, an LED lamp with a small emitting surface, so that an electromagnetic beam irradiated by it reaches a small spot of light in one focus. Such properties are fulfilled, for example, by small so-called SMD LEDs which have no lens housing and no reflector ring.

The dichroic mirrors can be regarded as high passes which transmit longer wave electromagnetic beams and reflect shorter wave beams. They are optimised to an impact angle of the electromagnetic beam of 45°. Their task is to divide up the two fluorescences spectrally and couple electromagnetic beams from the LED into the common main optical path.

These mirrors use dichroic coatings for dividing the incidence energy into two or more beams, each of which has a different wavelength.

The measurement or investigation and/or control of the fluorescence meter and the evaluation of the measurements obtained are achieved by the computer using the software or a suitable computer program. This computer program or this software is capable of carrying out all the steps of a process according to the invention for measuring fluorescence with the fluorescence meter by means of a suitable apparatus which comprises the computer or a corresponding computing unit. The software can be installed in any desired computer and it is envisaged that the software should be stored on a CD ROM which is to be placed in the computer so that the software from the CD ROM is stored as a computer program product on the computer, particularly on a hard disc of the computer. The computer is connected via at least one suitable interface to the apparatus or to the fluorescence meter for investigating or measuring the specimen and optionally to other instruments needed for the investigation, so that both regulation or control data and also measured data can be exchanged between the apparatus or the fluorescence meter and the computer.

Using the meter according to the invention it is possible to carry out measurements in 500 µl PCR tubes of $1.0 \times 10^{-12}$ M and in 200 µl PCR tubes of $2 \times 10^{-11}$ M. With a 1 cm² dish a measurement of $5 \times 10^{-13}$ M is possible. This is a fluorescein solution.

I claim:

1. Fluorescence meter for investigating a specimen, comprising:
    a housing including a main channel for a main optical path;
    a first source for providing an output comprising a first excitation electromagnetic beam disposed along the main optical path to excite the specimen;
        a monitor diode disposed near said first source to monitor the output of said first source for deviation from a desired value such that the output can be stabilized;
        a first sensor to detect an emitted electromagnetic beam from the specimen having a first spectral range;
        a first optical module to direct the emitted electromagnetic beam to said first sensor;
    said first optical module is configured such that the emission electromagnetic beam is disposed with the excitation electromagnetic beam at least partly in one plane and extending along the main optical path;
    a first band-pass filter disposed between said first source and the specimen;
    a second band-pass filter disposed between said first source and said monitor diode, said second band-pass filter not forming a part of an optical path between said first source and the specimen, an optical path between said first source and said monitor diode not including a beam splitter; and
    said first and second band-pass filters have the same optical properties such that the electromagnetic beam shining on the specimen and on said monitor diode is the same, whereby the output can be monitored and said first source can be stabilized.

2. Fluorescence meter according to claim 1, and further comprising:
    a second sensor to detect an emitted electromagnetic beam from the specimen having a second spectral range; and
    a second optical module to direct the emitted electromagnetic beam having the second spectral range to said second sensor.

3. Fluorescence meter according to claim 2, wherein said first sensor is configured to detect reflection.

4. Fluorescence meter according to claim 2, wherein:
    said housing includes a first secondary channel branching from said main channel, said first secondary channel for providing a first secondary optical path;
    an excitation optical module including a first beam splitter;
    said first source is disposed in said first secondary channel; and
    said first beam splitter is disposed in said main channel to deflect the first excitation electromagnetic beam into the main optical path.

5. Fluorescence meter according to claim 4, wherein:
    said housing includes a second secondary channel branching from said main channel, said second secondary channel for providing a second secondary optical path;
    said first sensor is disposed in said second secondary channel;
    said first optical module includes a second beam splitter; and
    said second beam splitter is disposed in said main channel to deflect the emission excitation electromagnetic beam having a first spectral range from the main optical path into the second secondary optical path.

6. Fluorescence meter according to claim 5, wherein:
    said housing includes a third secondary channel branching from said main channel, said third secondary channel for providing a third secondary optical path;
    said second sensor is disposed in said third secondary channel;
    said second optical module includes a third beam splitter; and
    said third beam splitter is disposed in said main channel to deflect the emission excitation electromagnetic beam having a second spectral range from the main optical path into the third secondary optical path.

7. Fluorescence meter according to claim 6, wherein said first, second and third beam splitters are dichroic mirrors.

8. A fluorescence meter according to claim 4, and further comprising a light trap disposed along said first secondary optical path beyond said first beam splitter.

9. Fluorescence meter according to claim 2, and further comprising a second source for providing another output comprising a second excitation electromagnetic beam disposed along the main optical path to excite the specimen.

10. Fluorescence meter according to claim 9, wherein:
    said first sensor is configured to detect a first fluorescence emission from the specimen; and
    said second sensor is configured to detect a second fluorescence emission from the specimen.

11. A fluorescence meter according to claim 9, wherein:
    the first excitation electromagnetic beam is a measuring beam; and
    the second excitation electromagnetic beam is a positioning beam to position the measuring beam from the specimen.

12. A fluorescence meter according to claim 2, and further comprising:
    a second source for providing another output comprising a second excitation electromagnetic beam disposed along the main optical path to excite the specimen;
    said housing includes a secondary channel branching from said main channel, said secondary channel for providing a secondary optical path;
    an excitation optical module including a first beam splitter;
    said second source is disposed in said secondary channel;
    said first beam splitter is disposed in said main channel to deflect the second excitation electromagnetic beam into the main optical path; and
    a light trap disposed along said secondary optical path beyond said first beam splitter.

13. Fluorescence meter according to claim 1, and further comprising a marking within said housing for an eye to concentrate on during examination.

14. Fluorescence meter according to claim 13, and further comprising an illumination source to provide a background illumination for said marking.

15. Fluorescence meter according to claim 1, wherein said first source is encapsulated with an encapsulation.

16. Fluorescence meter according to claim 15, wherein said encapsulation is an aluminum block.

17. Fluorescence meter according to claim 15, wherein said encapsulation has an opening.

18. Fluorescence meter according to claim 1, wherein said monitor diode is disposed within said housing to prevent light entering said housing from the outside through said main channel from hitting said monitor diode.

19. Fluorescence meter according to claim 1, and further comprising an adaptor for taking surface measurements from a dish, test strip, microscope slide or PCR tube.

20. Fluorescence meter for investigating a specimen, comprising:
   a housing including a main channel for a main optical path;
   a first source for providing an output comprising a first excitation electromagnetic beam disposed along the main optical path to excite the specimen;
   a monitor diode disposed near said first source to monitor the output of said first source for deviation from a desired value such that the output can be stabilized;
   a band-pass filter disposed between said first source and said monitor diode, said band-pass filter not forming a part of an optical path between said first source and the specimen, an optical path between said first source and said monitor diode not including a beam splitter;
   a second source separate from said first source, said second source for providing another output comprising a second excitation electromagnetic beam disposed along the main optical path to excite the specimen;
      a first sensor to detect an emitted electromagnetic beam having a first spectral range from the specimen;
      a second sensor to detect an emitted electromagnetic beam having a second spectral range from the specimen;
      a first optical module to direct the emitted electromagnetic beam having the first spectral range to said first sensor;
      a second optical module to direct the emitted electromagnetic beam having the second spectral range to said second sensor; and
   said first and second optical modules are configured such that the emission electromagnetic beams are disposed with the excitation electromagnetic beams at least partly in one plane and extending along the main optical path.

21. Fluorescence meter for investigating a specimen, comprising:
   a housing including a main channel for a main optical path;
   a first source for providing an output comprising a first excitation electromagnetic beam disposed along the main optical path to excite the specimen;
      a monitor diode disposed near said first source to monitor the output of said first source for spectral drift such that a change in output caused by the spectral drift can be adjusted;
      a first sensor to detect an emitted electromagnetic beam from the specimen having a first spectral range;
      a first optical module to direct the emitted electromagnetic beam to said first sensor;
   said first optical module is configured such that the emission electromagnetic beam is disposed with the excitation electromagnetic beam at least partly in one plane and extending along the main optical path;
   a first band-pass filter disposed in front of said first source;
   a second band-pass filter disposed between said first source and said monitor diode, said second band-pass filter not forming a part of an optical path between said first source and the specimen, an optical path between said first source and said monitor diode not including a beam splitter; and
   said first and second band-pass filters have the same optical properties such that the electromagnetic beam shining on the specimen and on said monitor diode is the same, whereby the output can be monitored and said first source can be adjusted.

* * * * *